United States Patent [19]
Carol

[11] Patent Number: 5,802,136
[45] Date of Patent: *Sep. 1, 1998

[54] METHOD AND APPARATUS FOR CONFORMAL RADIATION THERAPY

[75] Inventor: Mark P. Carol, Sewickley, Pa.

[73] Assignee: Nomos Corporation, Sewickley, Pa.

[*] Notice: The term of this patent shall not extend beyond the expiration date of Pat. No. 5,596,619.

[21] Appl. No.: 634,785

[22] Filed: Apr. 19, 1996

Related U.S. Application Data

[63] Continuation-in-part of Ser. No. 245,626, May 17, 1994, Pat. No. 5,596,619.

[51] Int. Cl.$^6$ ............................................. A61N 5/10
[52] U.S. Cl. ............................................. 378/65; 378/150
[58] Field of Search ................................. 378/65, 150

[56] References Cited
U.S. PATENT DOCUMENTS 5,596,619  1/1997  Carol ............................................. 378/65

*Primary Examiner*—Craig E. Church
*Attorney, Agent, or Firm*—Tobor & Goldstein, LLP

[57] ABSTRACT

A method and apparatus for conformal radiation therapy, with a radiation beam having a predetermined, constant beam intensity, treats the entire tumor volume of a patient's tumor, and the beam intensity of the radiation beam is spatially modulated across the tumor, by separating the radiation into an array of at least 3×3 treatment beam segments and independently modulating the beam intensity of the plurality of radiation beam segments. The independent modulation of the beam intensities may be accomplished by selectively and independently filling, or removing, a flowable, radiation blocking material from a compartment associated with each radiation beam segment.

33 Claims, 15 Drawing Sheets

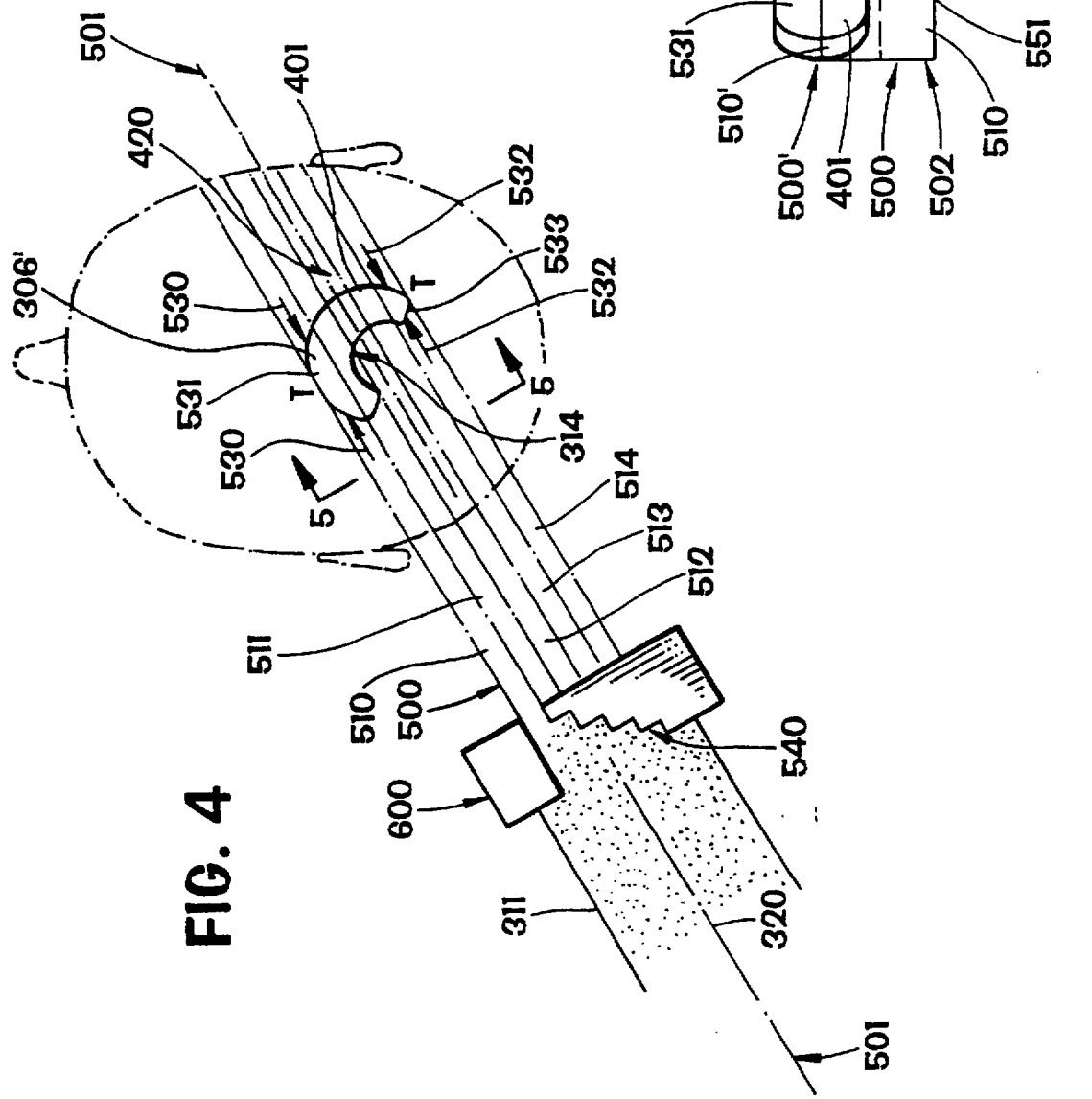

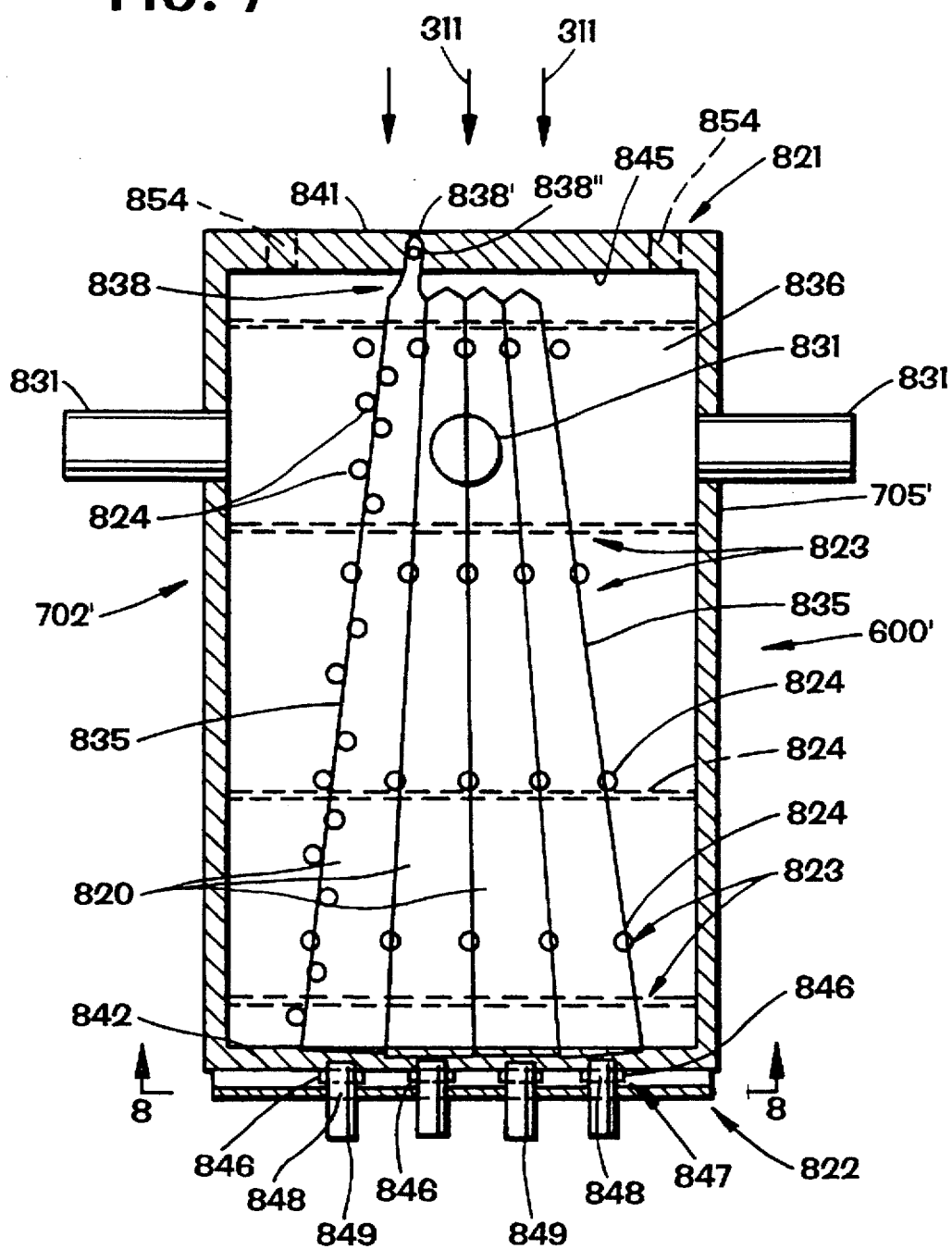

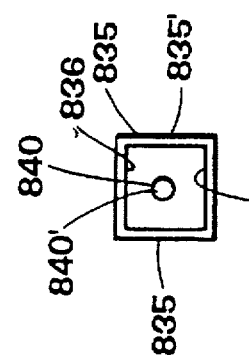
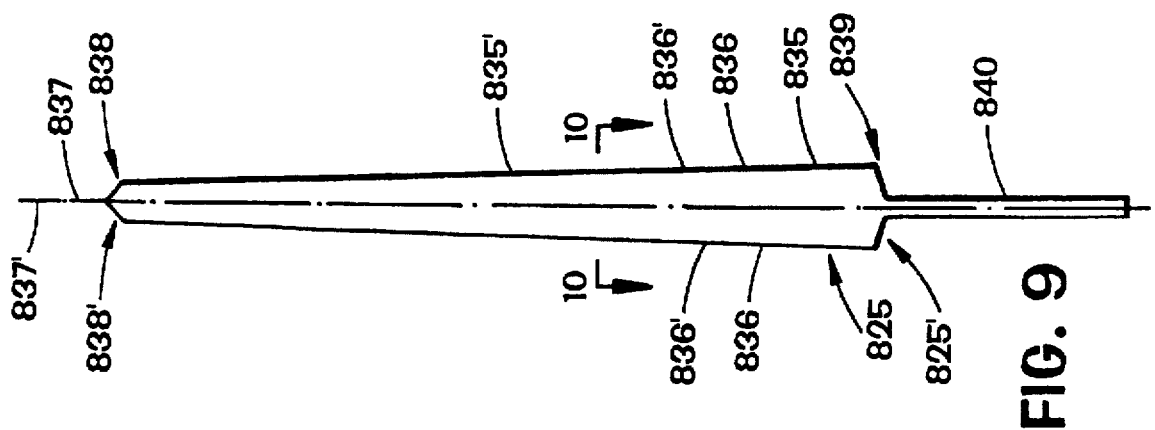
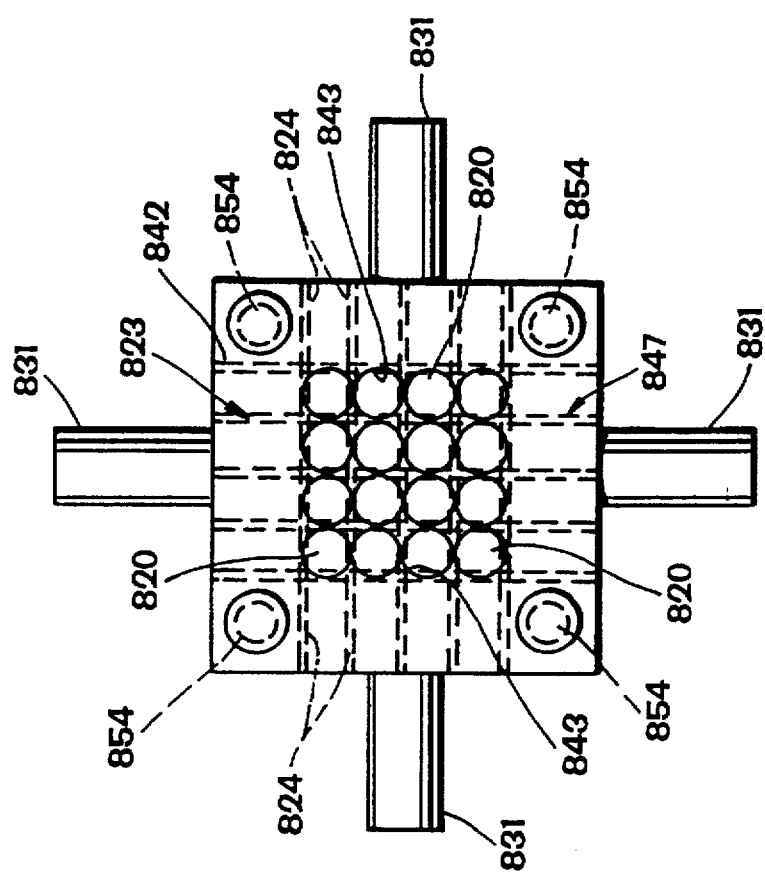

METHOD AND APPARATUS FOR CONFORMAL RADIATION THERAPY

RELATED APPLICATION

This application is a continuation-in-part of U.S. application Ser. No. 08/245,626, filed May 17, 1994 now U.S. Pat. No. 5,596,619.

BACKGROUND OF THE INVENTION

1. Field of the Invention

The invention relates to a method and apparatus for conformal radiation therapy of tumors with a radiation beam having a predetermined, constant beam intensity.

2. Description of the Prior Art

Modern day radiation therapy of tumors has two goals: eradication of the tumor and avoidance of damage to healthy tissue and organs present near the tumor. It is known that a vast majority of tumors can be eradicated completely if a sufficient radiation dose is delivered to the tumor volume; however, complications may result from use of the necessary effective radiation dose, due to damage to healthy tissue which surrounds the tumor, or to other healthy body organs located close to the tumor. The goal of conformal radiation therapy is to confine the delivered radiation dose to only the tumor volume defined by the outer surfaces of the tumor, while minimizing the dose of radiation to surrounding healthy tissue or adjacent healthy organs.

Conformal radiation therapy has been traditionally approached through a range of techniques, and typically uses a linear accelerator as the source of the radiation beam used to treat the tumor. The linear accelerator typically has a radiation beam source which is rotated about the patient and directs the radiation beam toward the tumor to be treated. The beam intensity of the radiation beam is a predetermined, constant beam intensity. Multileaf collimators, which have multiple leaf, or finger, projections which can be moved individually into and out of the path of the radiation beam, can be programmed to follow the spatial contour of the tumor as seen by the radiation beam as it passes through the tumor, or the "beam's eye view" of the tumor during the rotation of the radiation beam source, which is mounted on a rotatable gantry of the linear accelerator. The multiple leaves of the multileaf collimator form an outline of the tumor shape as presented by the tumor volume in the direction of the path of travel of the radiation beam, and thus block the transmission of radiation to tissue disposed outside the tumor's spatial outline as presented to the radiation beam, dependent upon the beam's particular radial orientation with respect to the tumor volume.

Another approach to conformal radiation therapy involves the use of independently controlled collimator jaws which can scan a slit field across a stationary patient at the same time that a separate set of collimator jaws follows the target volume as the gantry of the linear accelerator rotates. An additional approach has been the use of attachments for linear accelerators which allow a slit to be scanned across the patient, the intensity of the radiation beam in the entire slit being modified as the slit is being scanned.

A further approach for conformal radiation therapy treatment has been the use of a narrow pencil beam of high energy photons, whose energy can be varied, and the beam is scanned over the tumor target volume so as to deliver the best possible radiation dose distribution in each orientation of the gantry upon which the photon beam source is mounted.

A major problem associated with such prior art methods of conformal radiation therapy are that if the tumor volume has concave borders, or surfaces, varying the spatial configuration, or contour, of the radiation beam, is only successful part of the time. In particular, when the convolutions, or outer surfaces, of a tumor are re-entrant, or concave, in a plane parallel to the path of the radiation treatment beam, healthy tissue or organs may be disposed within the concavities formed by the outer tumor concave surfaces, as well as the fact that the thickness of the tumor varies along the path of the radiation beam.

In order to be able to treat tumors having concave borders, it is necessary to vary the intensity of the radiation beam across the surface of the tumor, as well as vary the outer configuration of the beam to conform to the shape of the tumor presented to the radiation beam. The beam intensity of each radiation beam segment should be able to be modulated to have a beam intensity related to the thickness of the portion of the tumor through which the radiation beam passes. For example, where the radiation beam is to pass through a thick section of a tumor, the beam intensity should be higher than when the radiation beam passes through a thin section of the tumor.

Dedicated scanning beam therapy machines have been developed wherein beam intensity modulation can be accomplished through the use of a scanning pencil beam of high energy photons. The beam intensity of this device is modulated by increasing the power of its electron gun generating the beam. The power increase is directed under computer control, as the gun is steered around the tumor by moving the gantry upon which it is mounted and the table upon which the patient lies. The effect is one of progressively "painting" the target with the thickness, or intensity, of the paint, or radiation beam intensity, being varied by the amount of paint on the brush, or how much power is applied to the electron gun, as the electron gun moves over the tumor. Such dedicated scanning beam therapy machines, which utilize direct beam energy modulation, are expensive and quite time consuming in their use and operation, and are believed to have associated with them a significant patient liability due to concerns over the computer control of the treatment beam itself.

Other methods and apparatus for conformal radiation therapy have been developed that spatially modulate the beam intensity of a radiation beam across a volume of tissue in accordance with the thickness of the tumor in the volume of tissue by utilizing a plurality of radiation beam segments. Such methods and apparatus utilize attenuating leaves, or shutters, in a rack positioned within the radiation beam before the beam enters the patient. The tumor is exposed to radiation in slices, each slice being selectively segmented by the shutters. However, a minor disadvantage of that method and apparatus results from the fact that only two slices of tissue volume may be treated with one rotation of the gantry of the linear accelerator. Although the slices may be of arbitrary thickness, greater resolution is accomplished by selecting slices for treatment that are as thin as possible. As the thickness of the treatment slices decreases, the time it takes to treat the patient increases because more treatment slices are required in order to treat the entire tumor volume.

Accordingly, prior to the development of the present invention, there has been no method or apparatus for conformal radiation therapy, for use with a radiation beam having a predetermined, constant beam intensity for treatment of a tumor which: are simple and economical to use; have what is believed to be a high safety factor for patient safety; and spatially modulate the radiation beam's intensity across the surface of the tumor presented to the radiation beam, or across the cross-sectional configuration of the radiation beam.

Therefore, the art has sought a method and apparatus for conformal radiation therapy, for use with a radiation beam having a predetermined, constant beam intensity for treatment of a tumor which: are simple and economical to use; have what is believed to be a high safety factor to provide the patient with a high degree of safety during treatment; and permit the radiation beam's intensity to be spatially modulated across the tumor or across the cross-sectional configuration of the radiation beam.

SUMMARY OF INVENTION

In accordance with the invention, the foregoing advantages have been achieved through the present apparatus for use in conformal radiation therapy of a tumor, comprising: a radiation beam source for producing a radiation beam having a predetermined, constant beam intensity; at least a 3×3 checkerboard array having alternating radiolucent and radiopaque compartments, for separating the radiation treatment beam into an array of a plurality of beam segments; and means for independently modulating the beam intensity of the radiation beam segments to spatially modulate the beam intensity of the radiation treatment beam across the tumor.

In accordance with another aspect of the invention, the foregoing advantages have also been achieved through the present apparatus for use in conformal radiation therapy of a tumor, comprising: a radiation beam source for producing a radiation beam having a predetermined, constant beam intensity; a checkerboard array of a plurality of spaced-apart, radiopaque, compartments having walls, at least a portion of a wall of each of four of the solid compartments defining a radiolucent compartment between the four solid compartments, for separating the radiation treatment beam into an array of a plurality of beam segments; and means for independently modulating the beam intensity of the radiation beam segments to spatially modulate the beam intensity of the radiation treatment beam across the tumor.

In accordance with another aspect of the invention, the foregoing advantages have also been achieved through the present method of conformal radiation therapy, with a radiation beam having a predetermined, constant beam intensity for treatment of a volume of tissue in a patient, the volume of tissue containing a tumor to be treated, the tumor having a total tumor volume and a varying thickness, comprising the steps of: directing the radiation treatment beam toward the volume of tissue; separating the radiation treatment beam into an array of at least 3×3 beam segments; and independently modulating the beam intensity of at least one of the beam segments to spatially modulate the beam intensity of the radiation treatment beam across the volume of tissue, to treat the tumor with the beam segments, each radiation beam segment having a predetermined beam intensity.

Another feature of this aspect of the present invention may include the steps of: rotating the radiation beam about the patient to successively direct the plurality of radiation beam segments toward the volume of tissue; and modulating the beam intensity of the at least one of the radiation beam segments independent of at least one other of the radiation beam segments, to spatially modulate the beam intensity of the radiation treatment beam across the volume of tissue as the plurality of radiation beam segments are directed toward the volume of tissue. An additional feature of this aspect of the present invention may include the step of rotating the radiation beam in specified degree segments of a radial arc to treat the volume of tissue after each such rotation of the radiation beam.

Another feature of this aspect of the present invention may include the step of: the at least one radiation beam being separated into a plurality of radiation beam segments by passing the radiation beam through an array of at least 3×3 compartments extending through a housing, having a top and a bottom, each compartment defining a passageway for a radiation beam segment. An additional feature of this aspect of the present invention may further include the step of: the at least one radiation beam being separated into a plurality of radiation beam segments by passing the radiation beam through an array of at least 3×3 compartments extending through a housing, having a top and a bottom, at least four compartments being closed and comprising radiopaque blocks, having walls, in a checkerboard arrangement, the walls of the radiopaque blocks defining at least one radiolucent, or open, compartment providing a passageway for a radiation beam segment.

An additional feature of this aspect of the present invention may further include the steps of: providing the housing with a quantity of flowable, radiation blocking material in communication with the radiolucent, or open, compartments; and the beam intensities of each radiation beam segment may be modulated by selectively filling at least a portion of a radiolucent, or open, compartment with the flowable, radiation blocking material or removing at least a portion of the flowable, radiation blocking material from a radiolucent, or open, compartment.

Another feature of this aspect of the present invention may include the step of independently varying the amount of time each compartment is selectively filled with the flowable, radiation blocking material. An additional feature of this aspect of the present invention may include the step of selectively, substantially completely filling a radiolucent, or open, compartment with the flowable, radiation blocking material or substantially completely removing the flowable, radiation blocking material from a compartment. A feature of this aspect of the present invention may further include the step of utilizing mercury as the flowable, radiation blocking material. Another feature of this aspect of the present invention may further include the steps of: providing an expandable, radiolucent member in each radiolucent, or open, compartment; and expanding the radiolucent members within preselected compartments to remove at least a portion of the flowable, radiation blocking material from the preselected compartments.

An additional feature of this aspect of the present invention may further include the steps of: utilizing inflatable balloons as the expandable, radiolucent members; and expanding the inflatable balloons with a source of pressurized fluid. Yet another feature of this aspect of the present invention may further include the steps of providing each radiolucent, or open, compartment with a substantially square cross-sectional configuration; and providing each expandable, radiolucent member, when expanded, with a substantially square cross-sectional configuration substantially conforming to the cross-sectional configuration of the compartments. Another feature of this aspect of the present invention may include the step of increasing the size of the cross-sectional configuration of each compartment and each expandable, radiolucent member, when expanded, from the top of the housing to the bottom of the housing.

Another feature of this aspect of the present invention may further include the steps of: utilizing inflatable balloons as the expandable, radiolucent members; and disposing each inflatable balloon in fluid communication with a source of pressurized fluid. An additional feature of this aspect of the present invention may further include the step of selectively inflating and deflating the inflatable balloons.

In accordance with another aspect of the invention, the foregoing advantages have also been achieved through the present method of conformal radiation therapy, with a radiation beam having a predetermined, constant beam intensity for treatment of a volume of tissue in a patient, the volume of tissue containing a tumor to be treated, the tumor having a total tumor volume and a varying thickness, comprising the steps of: directing the radiation treatment beam toward the volume of tissue; treating a first portion of the tumor by separating the radiation treatment beam into an array of at least 3×3 beam segments, independently modulating the beam intensity of at least one of the beam segments to spatially modulate the beam intensity of the radiation treatment beam across the volume of tissue, each radiation beam segment having a predetermined beam intensity; and treating a second portion of the tumor by separating the radiation treatment beam into an array of at least 3×3 beam segments, independently modulating the beam intensity of at least one of the beam segments to spatially modulate the beam intensity of the radiation treatment beam across the volume of tissue, each radiation beam segment having a predetermined beam intensity.

An additional feature of this aspect of the present invention may include the steps of: rotating the radiation beam about the patient to successively direct the plurality of radiation beam segments toward the volume of tissue; and modulating the beam intensity of the at least one of the radiation beam segments independent of at least one other of the radiation beam segments, to spatially modulate the beam intensity of the radiation treatment beam across the volume of tissue as the plurality of radiation beam segments are directed toward the volume of tissue. Another feature of this aspect of the present invention may include the at least one radiation beam being separated into a plurality of radiation beam segments by passing the radiation beam through an array of at least 3×3 compartments extending through a housing, having a top and a bottom, each compartment defining a passageway for a radiation beam segment.

Another feature of this aspect of the present invention may also include the at least one radiation beam being separated into a plurality of radiation beam segments by passing the radiation beam through an array of at least 3×3 compartments extending through a housing, having a top and a bottom, at least four compartments being closed by radiopaque blocks, having walls, the radiopaque blocks being disposed in a checkerboard arrangement, with the walls of the radiopaque blocks defining at least one radiolucent, or open, compartment providing a passageway for a radiation beam segment.

An additional feature of this aspect of the present invention may include the step of treating a second portion of the tumor by the steps of rotating the array of at least 3×3 compartments 90 degrees and providing the housing with a quantity of flowable, radiation blocking material in communication with the radiolucent, or open, compartments, and wherein the beam intensities of each radiation beam segment are modulated by selectively filling at least a portion of a radiolucent, or open, compartment with the flowable, radiation blocking material or removing at least a portion of the flowable, radiation blocking material from a radiolucent, or open, compartment.

Another feature of this aspect of the present invention may be that the step of treating the second portion of the tumor may include the steps of rotating the array of at least 3×3 compartments 180 degrees and providing the housing with a quantity of flowable, radiation blocking material in communication with the radiolucent, or open, compartments, and wherein the beam intensities of each radiation beam segment are modulated by selectively filling at least a portion of a radiolucent, or open, compartment with the flowable, radiation blocking material or removing at least a portion of the flowable, radiation blocking material from a radiolucent, or open, compartment.

Another feature of this aspect of the present invention may be that the step of treating the second portion of the tumor includes the steps of shift indexing the array of at least 3×3 compartments and providing the housing with a quantity of flowable, radiation blocking material in communication with the radiolucent, or open, compartments, and wherein the beam intensities of each radiation beam segment are modulated by selectively filling at least a portion of a radiolucent, or open, compartment with the flowable, radiation blocking material or removing at least a portion of the flowable, radiation blocking material from a radiolucent, or open, compartment.

In accordance with another aspect of the invention, the foregoing advantages have also been achieved through the present apparatus for use in conformal radiation therapy of a tumor with a radiation beam from a radiation beam source, the radiation beam having a predetermined, constant beam intensity, comprising: means for separating the radiation treatment beam into a plurality of radiation beam segments, including a housing having a top and a bottom; the housing containing an array of at least 3×3 compartments, extending from the top to the bottom of the housing, each compartment defining a passageway for a radiation beam segment; and means for independently modulating the beam intensity of the plurality of radiation beam segments to spatially modulate the beam intensity of the radiation treatment beam across the tumor.

Another feature of this aspect of the present invention may be that the means for separating the radiation treatment beam into a plurality of radiation beam segments includes: a housing having a top and a bottom; the housing containing an array of at least 3×3 compartments, extending from the top to the bottom of the housing, at least four compartments being closed and comprising radiopaque blocks, having walls, in a checkerboard arrangement, the walls of the radiopaque blocks defining at least one open passageway for a radiation beam segment.

Another feature of this aspect of the present invention may be that the means for independently modulating the beam intensity of the plurality of radiation beam segments includes: an expandable, radiolucent member associated with each radiolucent, or open, compartment; a quantity of flowable, radiation blocking material disposed within the housing and within each radiolucent, or open, compartment when the expandable member associated with a radiolucent, or open, compartment is unexpanded; and a reservoir for the flowable, radiation blocking material, whereby upon expansion of the expandable member, the expandable member displaces the flowable, radiation blocking material outwardly from the radiolucent, or open, compartment associated with the expandable member and into the reservoir, so that a radiation beam segment may pass through the compartment toward a portion of the tumor.

An additional feature of this aspect of the present invention may also be that each compartment has a substantially square cross-sectional configuration and the expandable, radiolucent member associated with each radiolucent, or open, compartment, when expanded, has a substantially square cross-sectional configuration substantially conforming to the cross-sectional configuration of the radiolucent, or open, compartment.

An additional feature of this aspect of the present invention may also be that the size of the cross-sectional configuration of each compartment and each expandable, radiolucent member, when expanded, increases from the top of the housing to the bottom of the housing.

In accordance with yet another aspect of the invention, the foregoing advantages have also been achieved through the present apparatus for use in conformal radiation therapy of a tumor, comprising: a radiation beam source for producing a radiation beam having a predetermined, constant beam intensity; at least a 3×3 checkerboard array having alternating radiolucent and radiopaque compartments, for separating the radiation treatment beam into an array of a plurality of beam segments; and means for independently modulating the beam intensity of the radiation beam segments to spatially modulate the beam intensity of the radiation treatment beam across the tumor.

In accordance with still another aspect of the invention, the foregoing advantages have also been achieved through an apparatus for use in conformal radiation therapy of a tumor, comprising: a radiation beam source for producing a radiation beam having a predetermined, constant beam intensity; a checkerboard array of a plurality of spaced-apart, solid, radiopaque, compartments having walls, at least a portion of a wall of each of four of the solid compartments defining a radiolucent, or open, compartment between the four solid compartments, for separating the radiation treatment beam into an array of a plurality of beam segments; and means for independently modulating the beam intensity of the radiation beam segments to spatially modulate the beam intensity of the radiation treatment beam across the tumor.

The method and apparatus for conformal radiation therapy, with a radiation beam having a predetermined, constant beam intensity of the present invention, when compared with previously proposed prior art methods and apparatus, have the advantages of: being simple and economical to use; are believed to have a high safety factor to provide the patient with a high degree of safety while being treated; and permitting spatial modulation of the beam intensity of the radiation beam across the tumor and across the cross-sectional configuration of the radiation beam.

BRIEF DESCRIPTION OF THE DRAWINGS

In the drawings:

FIG. 4 is a partial cross-sectional view of a patient's head having a tumor disposed therein, this view being similar to FIG. 3E, illustrating the path of a radiation beam through a portion of a tumor in accordance with the present invention;

FIG. 5 is a front view of the tumor of FIG. 4 taken along line 5—5 of FIG. 4, and illustrating the spatial contour of the tumor as seen by a radiation beam;

FIG. 7 is a partial cross-sectional view of an apparatus for use in conformal radiation therapy;

FIG. 8 is a partial cross-sectional view of the apparatus of FIG. 7, taken along line 12—12 of FIG. 11;

FIG. 9 is a side view of an expandable, radiolucent member in accordance;

FIG. 10 is a cross-sectional view taken along line 14—14 of FIG. 9;

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION OF THE INVENTION

Figure 1:
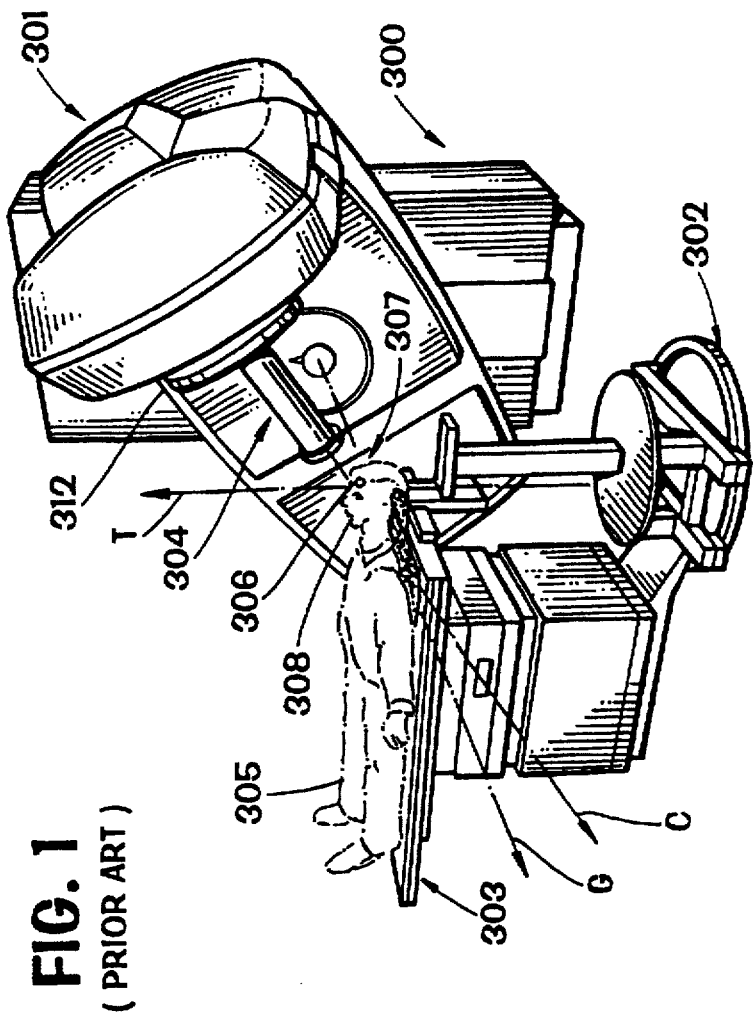
FIG. 1 is a perspective view conventional linear accelerator, including a rotatable couch, collimator and gantry.

With reference to FIG. 1, a conventional linear accelerator 300 is shown as including a gantry 301, turntable 302 which causes patient couch 303 to rotate therewith, and a conventional collimator 304. The three axes of rotation of the gantry 301, turntable and couch 302, 303, and collimator 304 are designated with the letters G, T, and C, respectively. As illustrated in FIG. 1, the patient 305 is disposed upon the rotatable couch 303 by use of a conventional stereotactic fixation device (not shown), or other conventional means for fixating the body to the patient couch 303. One type of fixation system that could be utilized is that disclosed in U.S. Pat. No. 5,163,430, entitled Method and Apparatus for Performing Stereotactic Surgery, in the name of the present inventor. As will be hereinafter described, it is necessary to conduct computerized tomographic ("CT") scanning of the patient prior to providing the conformal radiation therapy of the present invention. It is thus important that the patient be positioned properly on the patient couch 303, which position geometrically corresponds to the position the patient had on the imaging table (not shown) of the CT scanner. The device disclosed in the foregoing patent application provides the necessary positioning of the patient, and the correct positioning of the patient with respect to linear accelerator 300 and the CT scanner (not shown). The target, lesion, or tumor 306 is typically disposed at the isocenter 307 of the linear accelerator 300. The isocenter 307 is defined as the point of intersection of the three axes of rotation, C, G, and T of linear accelerator 300. The use of the term "tumor" herein encompasses any target, lesion, or tumor which is to be the subject of the conformal radiation therapy of the present invention. Although the tumor 306 described as being treated herein is disposed within the patient's skull 308, the method and apparatus of the present invention may be used to treat tumors located in any anatomical location in the patient's body.

The linear accelerator 300 produces a beam of radiation 311 (FIG. 4), made up of photons which generate gamma rays when they impinge upon human tissue, and the radiation beam 311 is focused and directed toward tumor 306. The radiation beam 311 exits from the conventional accelerator head 312, and then may pass through a conventional collimator 304, as it travels toward the tumor 306. The method and apparatus of the present invention may be also utilized with a conventional cobalt therapy device, or any other radiation device which produces a radiation beam 311 having a predetermined, constant beam intensity, such as linear accelerator 300 or a cobalt therapy device (not shown).

Figure 2A:
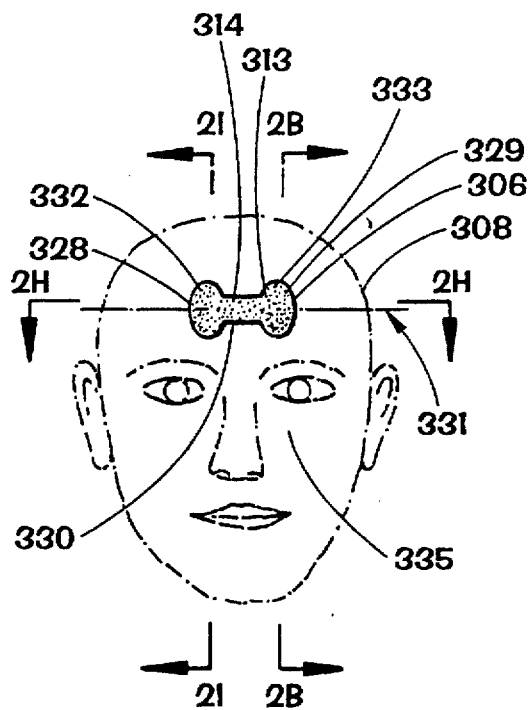
FIG. 2A is a partial cost-sectional front view of a patient's head, or skull, having a tumor disposed therein, taken along line 2A—2A of FIG. 2B.
Figure 2B:
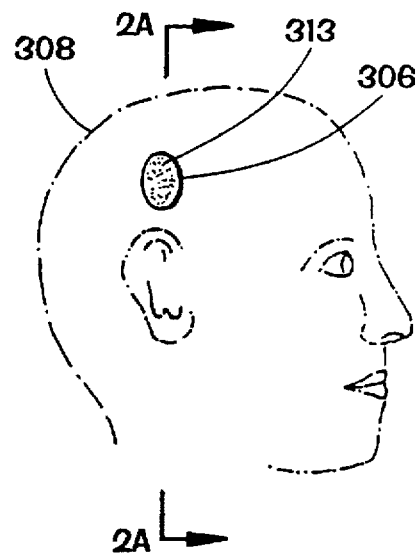
FIG. 2B is a partial cross-sectional side view of the same patient's head taken along line 2B—2B of FIG. 2A.
Figure 2C:
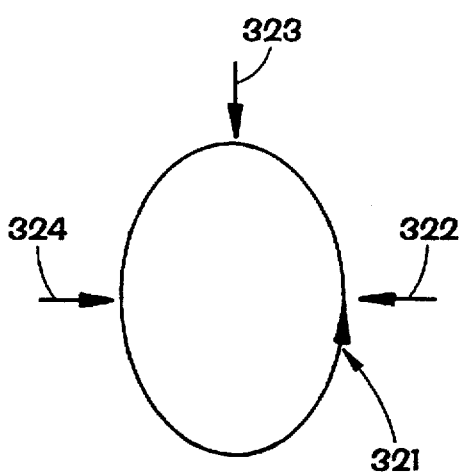
FIG. 2C is a schematic diagram indicating a path of travel of the gantry of the linear accelerator of FIG. 1.
Figure 2D:
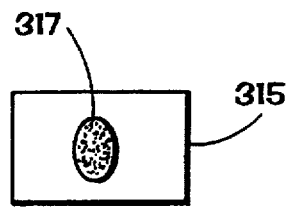
FIGS. 2D–2F are front views of conventional radiation compensator blocks used with the linear accelerator of FIG. 1.
Figure 2G:
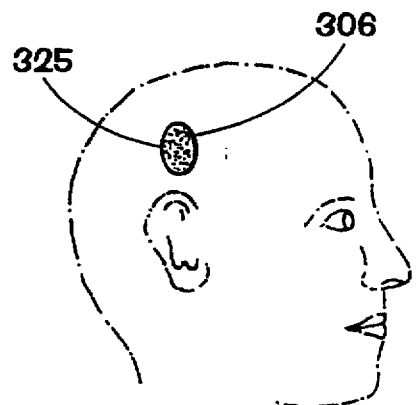
FIG. 2G is the same view as FIG. 2B, illustrating the spatial contour of the tumor as seen by a radiation beam as it passes through the compensator block of FIG. 2D, or the "beam's eye view" of the tumor.
Figure 2E:
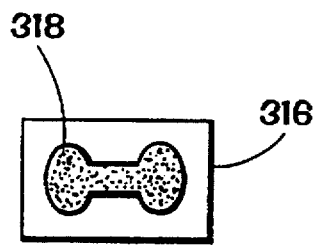
Figure 2F:
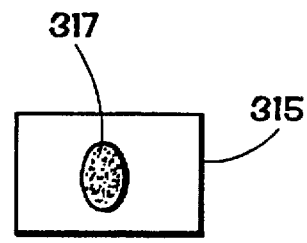

With reference to FIGS. 2A–2I, a conventional method of conformal radiation therapy is illustrated. As seen in FIGS. 2A and 2B, skull 308 has a tumor 306 disposed therein, tumor 306 having a total tumor volume which is encased by the outer surfaces 313 of tumor 306. Tumor 306 has concave surfaces 314 when viewed from the front as shown in FIG. 2A. Tumor 306 may also be referred to as "re-entrant in shape" because it "re-enters" itself or has concave surfaces 314. As shown in FIG. 2B, tumor 306 when viewed from the side of the patient's skull 308 has a generally oval-shaped configuration. When providing conventional radiation therapy treatment to tumor 306, a plurality of compensator blocks 315, 316 are formed and disposed between collimator 304 and the tumor 306, so as to conform the shape of the radiation beam 311 which passes through openings 317, 318 in compensator blocks 315, 316 to match the spatial contour of the tumor as seen by the radiation beam as it passes through the tumor, as the collimator 304 of linear accelerator 300 is rotated about the patient. The spatial contour of the tumor as seen by a radiation beam as it passes through the target is also generally referred to as the "beam's eye view", or what the shape of the tumor is when viewed along the longitudinal axis 320 of radiation beam 311 (FIG. 4), which axis is coplanar with the longitudinal axis of collimator 304. Compensator blocks 315, 316 are typically formed of a radiation shielding material, whereby the radiation beam is blocked from passing through such material, and may only pass through openings 317, 318 formed in compensator blocks 315, 316. In lieu of compensator blocks 315, 316, defining the desired spatial configuration of radiation beam 311 as illustrated in FIGS. 2D–2F, a conventional multileaf collimator may be used to provide openings which substantially correspond in shape with openings 317, 318.

Figure 2H:
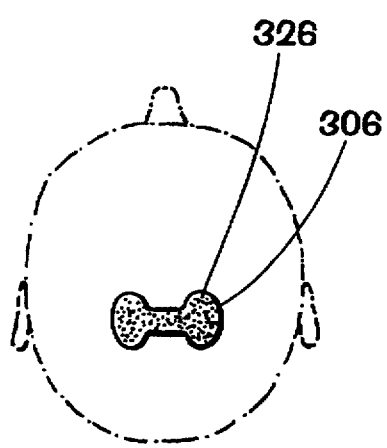
FIG. 2H is a partial cross-sectional view of the patient's head taken along line 2H—2H of FIG. 2A, and illustrates the spatial contour of the tumor as seen by a radiation beam as it passes through the compensator block of FIG. 2E.
Figure 2I:
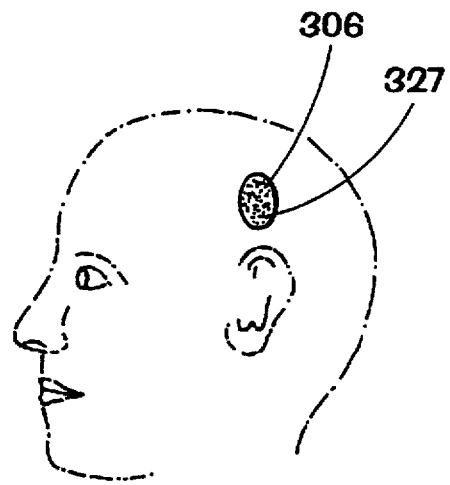
FIG. 2I is a partial cross-sectional view of the patient's head taken along line 2I—2I of FIG. 2A, and illustrates the spatial contour of the tumor as seen by a radiation beam as it passes through the compensator block of FIG. 2F.

Still with reference to FIGS. 2A–2I, tumor 306 is provided with radiation therapy utilizing compensator blocks 315, 316, while rotating gantry 301 in an ear-to-ear rotation as shown in FIG. 2C. Couch and turntable 303, 302, may be rotated 90 degrees from its position shown in FIG. 1, so that its longitudinal axis lies parallel with axis G of the gantry 301. Three radiation beams 322–324 may be directed toward tumor 306, beams 322, 324 toward the ears of the patient and beam 324 downwardly through the front of the patient's skull 308. When radiation beam 322 is directed toward skull 308 by accelerator head 312 and collimator 304, radiation beam 322 passes through opening 317 of compensator block 315 and travels toward tumor 306. The spatial contour 325 of tumor 306, as seen by radiation beam 322 as it passes through tumor 306, is shown in FIG. 2G. Upon rotation of gantry 301 through an arc of 90 degrees, linear accelerator 300 then generates radiation beam 323, which after passing through opening 318 in compensator block 316 travels through the front of the skull 308 and strikes target 306. The spatial contour 326 of the tumor 306, as seen by the radiation beam 323 as it passes through the tumor 306, or the beam's eye view of tumor 306, is illustrated in FIG. 2H. Upon further rotation of gantry 301 an additional 90 degree arc in the direction of arrow 321, radiation beam 324 passes through opening 317 in compensator block 315 of FIG. 2F and enters skull 308 and strikes target 306. The spatial contour 327 of the tumor 306 as seen by radiation beam 324 is shown in FIG. 2I.

In FIG. 2H, the radiation exposure to tumor 306 by radiation beam 323 corresponds to the actual spatial configuration of tumor 306 as illustrated in FIG. 2A. The resultant radiation exposure obtained from radiation beams 322, 324 would not correspond to the actual spatial configuration of the tumor 306 because tumor 306 is re-entrant or concave in a plane parallel to that of radiation beams 322, 324. The intensity of radiation beams 322, 324, are not varied to accommodate for the differing thickness of tumor 306 when the thickness is measured along the longitudinal axis 331 (FIG. 2A) of tumor 306.

For example, the tumor 306 has two enlarged end portions 328, 329 (FIG. 2A) and a smaller diameter central portion 330. As radiation beams 322, 324, pass through tumor 306 in the direction of its longitudinal axis 331 (FIG. 2A), portions of radiation beams 322, 324, will pass through differing thicknesses of tumor 306 along its longitudinal axis 331, because of concave surfaces 314, which result in the enlarged end portions 328, 329. Because the intensity of radiation beams 322, 324, typically remains constant, or in some instances might by varied across the entire spatial contour of the tumor as seen by the radiation beam, different portions of tumor 306 would receive an incorrect or insufficient dose of radiation. For example, the central portion of radiation beam 322 which passes through tumor 306 along its longitudinal axis 331, passes through end portions 328, 329 and central portion 330 of tumor 306. The upper portion of radiation beam 322 which only passes through the upper portions 332, 333 of the end portions 328, 329 of tumor 306, do not pass through the central portion 330 of tumor 306. Accordingly, the upper portion of radiation beam 322 passes through a total thickness of tumor tissue which is less than the thickness of tumor tissue along the longitudinal axis 331 of tumor 306. It is possible that the thicker volume of tumor tissue might not receive a large enough dose of radiation to be effective, whereas the thinner volume tumor tissue might receive a greater dose of radiation than is necessary to treat that portion of tumor 306, which in turn could damage surrounding healthy tissue 335.

With reference to FIGS. 3A–3F and 4–5, a method of conformal radiation therapy will be described. The same tumor 306 in patient's skull 308 will be treated with the linear accelerator 300 of FIG. 1. The radiation beam 311 from accelerator head, or radiation beam source, 312, of linear accelerator 300 has a predetermined, constant beam intensity, which will be used for treatment of a volume of tissue 400 (FIGS. 3D and FIG. 5), which volume of tissue 400 has at least a part 401, or first discrete portion 407, of tumor 306 disposed therein. The relative rotational motion between the patient's skull 308 and accelerator 312 may be provided in the same manner as previously described in connection with FIGS. 2A–2L. This method of conformal radiation therapy generally includes the steps of: directing the radiation beam 311 from a first position 405, as in the direction of arrow 406 (FIGS. 3A and 3C) toward a first discrete portion 407 of the tumor 306, which discrete portion 407 has a tumor volume less than the total tumor volume of the tumor 306; and spatially modulating the beam intensity of the radiation beam 311 over the first discrete portion 407 of the tumor 306, whereby the first discrete portion 407 of the tumor 306 receives a dose of radiation to treat the first discrete portion 407 of the tumor 306, while minimizing the irradiation of healthy tissue 335, which may be disposed adjacent to the tumor 306 and within volume of tissue 400. Preferably, the first discrete portion 407 of tumor 306 is disposed in a slice-shaped portion 411 of tissue volume 400. The use of the term "slice-shaped" is used as generally describing a thin flat piece of tissue.

As will be hereinafter described in greater detail, the total volume 450 of tissue of the patient containing the tumor 306 is divided, or separated, into a plurality of slice-shaped portions of tissue volume, four slice-shaped portions 411, 412, 413, 414 being illustrated in FIG. 3D. The first slice-shaped portion 411 of tissue volume 450 is illustrated in solid lines in FIG. 3D and FIG. 5, with slice-shaped portions 412–414 being illustrated in dotted lines in FIG. 3D. Each of the slice-shaped portions 411–414 of the total tissue volume 450 have a rectangular-shaped cross-sectional configuration in a plane disposed perpendicular to the longitudinal axis 320 of the radiation beam 311 in the direction of arrow 406, and the longitudinal axis 420 of slice-shaped portion 411 of tissue volume 400 is coplanar with the longitudinal axis of the radiation beam. As seen in FIG. 3D and FIG. 5, longitudinal axis 420 of slice-shaped portion 411 is disposed perpendicular to the plane upon which these figures appear, and is thus designated as a point 420.

Each of the slice-shaped portions 411–414 of the total tissue volume 450 are in an abutting relationship with their adjacent slice-shaped portions, and each slice-shaped portion 411–414 lie in planes which are parallel with each other and are coplanar with the longitudinal axis 320 of the radiation beam 311, in the direction of arrow 406. By rotating the radiation beam 311 about the patient 305, the radiation beam 311 may be directed from a second position 425 which is radially spaced from the first position 405. Radiation beam 311 is thus directed in the direction of arrow 426 (FIGS. 3A and 3C) toward the first discrete portion 407 of the tumor 306, which is disposed within another slice-shaped first portion 411' of the total tissue volume 450'. Slice-shaped portion 411' also has a rectangular-shaped cross-sectional configuration when viewed along the longitudinal axis 320 of radiation beam 311 when it is directed in the direction of arrow 426, as illustrated in FIGS. 3A and 3E. Likewise, as will be hereinafter described, additional slice-shaped portions 412'–414' are seen to lie in abutting relationship against their adjacent slice-shaped portions 411'–414', and these slice-shaped portions of the total tissue volume 450' lie in planes which are parallel with each other. When radiation beam 311 is directed toward tumor 306 along the direction of arrow 426, the beam intensity of the radiation beam is again spatially modulated over the discrete portion 407 of the tumor 306, whereby the first discrete portion 407 of the tumor receives another dose of radiation to treat the first discrete portion 407 of the tumor 306, while minimizing the irradiation of healthy tissue adjacent the tumor.

Figure 3C:
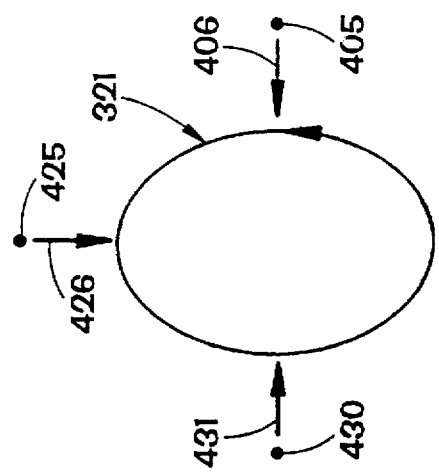
FIG. 3C is a schematic diagram illustrating the rotation of the gantry of the linear accelerator of FIG. 1.
Figure 3F:
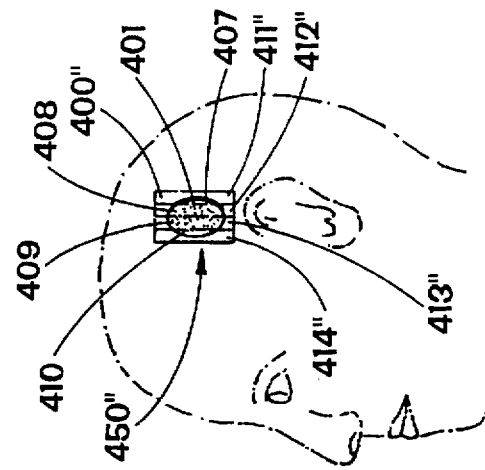
FIG. 3F is a partial cross-sectional side view of the patient's head taken along line 3F—3F of FIG. 3A, illustrating a method of conformal radiation therapy.
Figure 3B:
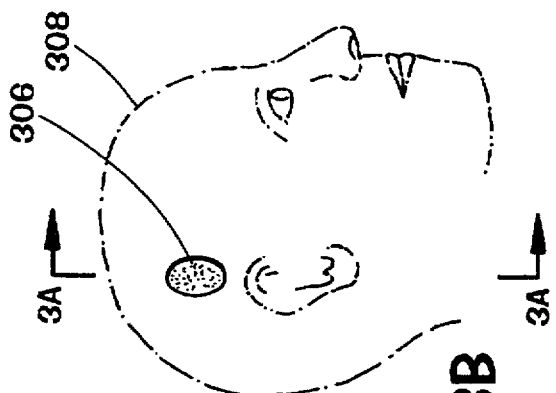
FIG. 3B is a partial cross-sectional side view of a patient's head taken along line 3B—3B of FIG. 3A.
Figure 3E:
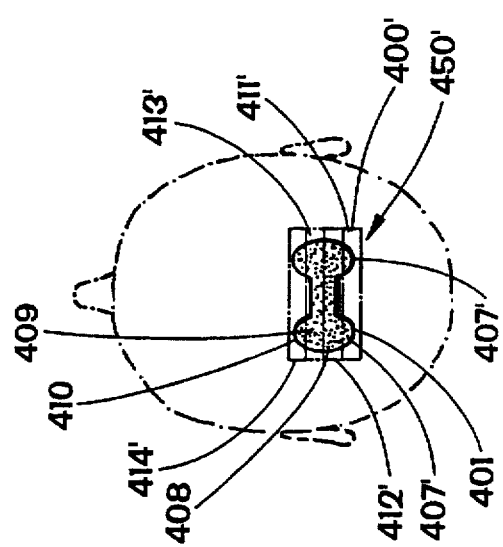
FIG. 3E is a partial cross-sectional top view of a patient's head taken along line 3E—3E of FIG. 3A illustrating a conformal radiation therapy method.
Figure 3A:
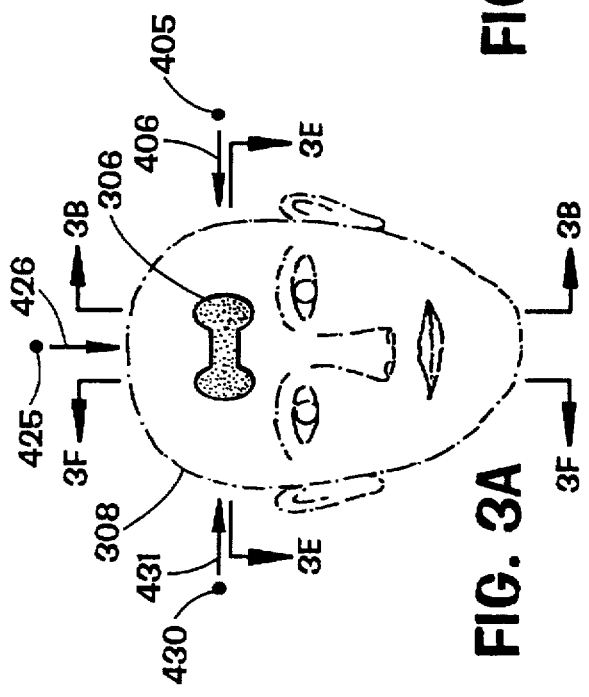
FIG. 3A is a partial cross-sectional front view of a patient's head having a tumor disposed therein, taken along line 3A—3A of FIG. 3B.
Figure 3D:
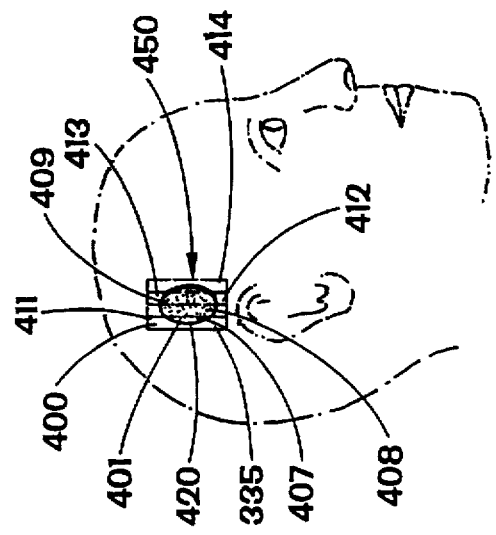
FIG. 3D is a partial cross-sectional side view of a patient's head of FIG. 3B illustrating a method of conformal radiation therapy.

Upon rotation of the radiation beam 311 to another position 430 radially spaced from the proceeding position 425, so as to direct the radiation beam 311 in the direction of arrow 431, toward tumor 306, another slice-shaped portion 411" has radiation beam 311 directed toward it as seen in FIG. 3F. Slice-shaped portion 411" of the total tissue volume 450" also has a rectangular cross-sectional configuration lying in a plane which is perpendicular to the longitudinal axis of the radiation beam, or in the direction of arrow 431. Additionally, slice-shaped portions 412'–414" of total tissue volume 450", as previously described, are also in abutting relationship with adjacent slice-shaped portion of total tissue volume 450" with each of the slice-shaped portions 411"–414" lying in parallel planes. Once again, the longitudinal axis of each of these slice-shaped portions 411"–414" are coplanar with the longitudinal axis of the radiation beam 311 acting upon it in the direction of arrow 431. When radiation beam 311 is directed in the direction of arrow 431 toward slice-shaped portions 411"–414" of total tissue volume 450", its beam intensity is spatially modulated over the first discrete portion 407 of tumor 306 disposed within slice-shaped portion 411' of tissue volume 400'. It should be noted that the slice-shaped portions 411, 411', 411" of total tissue volumes 450, 450', 450" are coplanar with each other, as is the case for slice-shaped portions: 412, 412', 412"; 413, 413', 413'; and 414, 414',414'.

After the first discrete portion 407 of tumor 306 has been treated in the manner previously described, the other discrete portions 408–410 of tumor 306 disposed within their respective slice-shaped portions 412, 412', 412"; 413, 413', 413"; 414, 414', 414", may be treated in turn in the manner previously described, whereby from each radially spaced location from which radiation beam 311 is directed toward tumor 306, the beam intensity of radiation beam 311 is spatially modulated over the discrete portion of tumor 306 being treated. The subsequent treatment of additional slice-shaped portions 412–414, 412'–414', 412"–414" may be accomplished by moving the patient with respect to the radiation beam source 311, or the accelerator head 312, a distance equal to the thickness of the slice-shaped portions of the tissue volume being treated. Upon successive rotations of the radiation beam 311 about the patient and movement of the patient with respect to the radiation beam source, as previously described, the entire tumor 306, or its entire tumor volume, contained within the total tissue volumes 450, 450', 450" may be properly treated by the radiation therapy. As will be hereinafter described, the number of slice-shaped portions of the total tissue volume being treated may be varied, as well as the thickness of each slice-shaped portion of tissue volume. Four slice-shaped portions of tissue volume were shown treated in FIGS. 3D–3F, which number of slice-shaped portions of tissue volume were selected for illustrative purposes only. Furthermore, it should be noted that the application of the radiation beam from only three locations 405, 425, 430, has also been used for illustrative purposes only, as will be hereinafter described in greater detail.

With reference to FIGS. 4 and 5, a simplified method of conformal radiation therapy will be described in further detail. Tumor 306' has a different configuration from that of tumor 306 illustrated in the preceding figures; however, it is also re-entrant in shape, having concave surfaces 314 as seen in FIG. 4, with concave surfaces 314' as viewed in FIG. 5. Radiation beam 311 is initially shaped into at least one radiation treatment beam 500 which has a longitudinal axis 501 which corresponds to the longitudinal axis 320 of radiation beam 311. Longitudinal axis 501 extends along the same path along which radiation beam 311 travels. Radiation treatment beam 500 has a rectangular-shaped cross-sectional configuration 502 which is disposed in a plane perpendicular to the longitudinal axis 501 of the radiation beam 311. As seen in FIG. 5, the rectangular-shaped cross-sectional configuration 502 of radiation treatment beam 500 corresponds to the rectangular-shaped cross-sectional configuration of the slice-shaped portion 411 of tissue volume 400 with the longitudinal axis 501 of the radiation treatment beam 500 being coplanar with the longitudinal axis 420 of slice-shaped portion 411 of tissue volume 400. Preferably, the rectangular cross-sectional configuration 502 of the at least one radiation treatment beam 500 is separated into a plurality of radiation beam segments 510–514, in a manner which will be hereinafter described. The beam intensity of the plurality of radiation beam segments 510–514 of the radiation treatment beam 500 are then independently modulated across the rectangular cross-sectional configuration 502 of the radiation treatment beam 500, whereby the first part 401 of the tumor 306', which has a varying thickness in a direction along the longitudinal axis 420 of the slice-shaped portion 411 of tissue volume 400, is treated by the plurality of radiation beam segments 510–514. Each radiation beam segment 510–514 of radiation treatment beam 500 may have a beam intensity in accordance with the thickness of the part 401 of tumor 306' through which each radiation beam segment 510–514 passes. For example, as seen in FIG. 4, arrows 530 denote the thickness T of one portion, or segment, 531 of the part 401 of tumor 306', through which radiation beam segment 510 of radiation treatment beam 500 passes. Arrows 532 denote the thickness T' of a portion 533 of the part 401 of tumor 306' through which radiation beam segment 514 passes. Since the thickness T of tumor segment 531 is greater than the thickness T' of tumor segment 533, the beam intensity of radiation beam segment 510 may be greater than the beam intensity of radiation beam segment 514, in order to properly treat tumor segments 531, 533 with radiation treatment beam 500. However, the beam intensity may be selected independent of the thickness of a particular portion of a tumor.

In FIG. 4, a means for independently modulating 600 the beam intensities of the plurality of radiation beam segments 510–514 is schematically illustrated to provide the spatial modulation of the beam intensity of the radiation treatment beam 500 across its rectangular cross-sectional configuration 502. A preferred form of independent beam modulation means 600 from that shown in FIG. 4 will be hereinafter described. For purposes of understanding the method of the present invention, as schematically illustrated in FIG. 4, a simplified version of independent modulation of the beam intensities of the plurality of radiation beam segments 510–514 is illustrated by disposing differing thicknesses of a radiation attenuation material between radiation beam 311 and radiation treatment beam 500. For example, since the thickness T of segment 531 of the part 401 of tumor 306' is the thickest portion of the part 401 of tumor 306' being treated within the volume of tissue 400, the path of radiation beam 311 through beam intensity modulation means 600 is open, whereby the beam intensity of radiation beam segment 510 treating tumor segment 531 is the same predetermined, constant beam intensity of radiation beam 311. Similarly, since segment 533 of tumor 306' is relatively thin in comparison with the other segments of part 401 of tumor 306', a relatively thick portion 540 of radiation attenuation, or blocking, material 540 is disposed in the path of radiation beam 311. The beam intensity of radiation beam segment 514 is thus reduced, commensurate with the necessary dose of radiation to properly treat segment 533 of tumor 306'. It should be noted that five radiation beam segments 510–514 have been shown for illustrative purposes only, as will be hereinafter described in greater detail. Additionally, it should be noted that any means for independently modulating 600 the beam intensity of the plurality of radiation beam segments 510–514 to spatially modulate the beam intensity of the radiation treatment beam 500 across its rectangular cross-sectional configuration 502 may be utilized in practicing the method of the present invention.

If desired, and as will be hereinafter described in greater detail, it is possible to shape the radiation beam 311 into an array of radiation treatment beams 500, 500'. FIG. 5 shows an array of 2×5 radiation beam segments 510–514, 510'–514'. However, in a preferred embodiment discussed below, an array of at least 3×3 radiation beam segments may be preferred. Radiation treatment beam 500 would comprise radiation beam segments 510–514, and radiation treatment beam 500' would comprise radiation treatments beam segments 510'–514'. Each radiation treatment beam 500, 500' would have a longitudinal axis extending along the path which the radiation treatment beams 500, 500' travel and have a rectangular-shaped cross-sectional configuration in a plane disposed perpendicular to the longitudinal axis 501 of the radiation treatment beams 500, 500'. Horizontal dotted line 550 in FIG. 5 is used to designate the abutting parallel surfaces of the two radiation treatment beams 500, 500' rectangular cross-sectional configurations, and the vertically disposed dotted lines 551 designate the abutting parallel surfaces of the adjacent radiation beam segments 510–514, 510'–514'. If only one radiation treatment beam 500 is shaped, radiation beam segments 510–514 would extend the entire distance from the bottom to the top of the rectangular cross-sectional configuration 502 of the radiation treatment beam 500.

If only one radiation treatment beam 500 is shaped, this radiation treatment beam 500, with its plurality of radiation beam segments 510–514 would be directed toward the first discrete portion 407 of tumor 306 in the first slice-shaped portions 411–411 " of tissue volume 400 as radiation beam 311 is rotated about the patient's skull 308, as previously described in connection with FIGS. 3D–3F. The patient would then be moved with respect to the radiation beam 311, a distance equal to the thickness of the slice-shaped portion 411 being treated, whereby the process would be repeated to treat the next plurality of slice-shaped portions 412–412". Each time the radiation treatment beam 500 is directed toward a slice-shaped portion of tissue, such as from positions 405, 425, 430, the beam intensity of the radiation beam segments 510–514 would be independently modulated, dependent upon the thickness of the tumor segment through which the radiation beam segment passes, as previously described. Preferably, radiation beam 311 is rotated about an arc of approximately 160 degrees in the direction of arrow 321 (FIG. 3C), and radiation beam 311 is turned on and directed toward the tumor, and its beam intensity modulated, after each specified degrees of rotation about the skull 308, or in specified degree segments of the 160 degree radial arc 5 degrees of rotation may be preferred in a particular application; but other increments may be used.

If the radiation beam 311 is shaped into two radiation treatment beams 500, 500', two adjacent slice-shaped portions of tissue, such as slice-shaped portions 411–411" and 412–412" may be simultaneously treated in the manner previously described. It would then be necessary to move the patient with respect to the radiation beam 311, or radiation beam source 312, a distance equal to the thickness of two slice-shaped portions of tissue, whereby another pair of adjacent slice-shaped portions of tissue may be treated, such as slice-shaped portions 413–413" and 414,414". As will be hereinafter described in greater detail, the control of the means for independently modulating 600 the beam intensity of the plurality of radiation beam segments 510–514 or the spatial modulation of the beam intensity of the radiation beam 311 across each of the plurality of slice-shaped portions of the tissue volume, is preferably controlled by a suitable computer system.

With reference to FIGS. 7–14, a method and apparatus 700' for conformal radiation therapy will be described. While previous methods and apparatus for conformal radiation therapy have proven to be effective in spatially and temporally modulating a linear accelerator beam in a slice-by-slice manner in order to produce intensity modulation conformal radiation therapy, a minor disadvantage of that method and apparatus may result from the fact that only a maximum of two slices of tissue volume may be treated with one rotation of the gantry of the linear accelerator. Although the slices may be of arbitrary thickness, greater resolution is accomplished by selecting slices for treatment that are as thin as possible. As the thickness of the treatment slices decreases, the time it takes to treat the patient increases because more treatment slices are required in order to treat the entire tumor volume.

The method and apparatus 700' and the method and apparatus 700" of the present invention, to be hereinafter described, treats an unlimited number of slices of the volume of tissue containing a tumor, and in many instances, dependent upon the size of the tumor, are able to treat the entire volume of tissue containing the tumor, with only one rotation of the gantry of the linear accelerator, thus decreasing the time necessary to treat the patient. The same reference numerals are used for elements previously described, and primed reference numerals are utilized for elements having functions and structures similar to those previously described.

Figure 11:
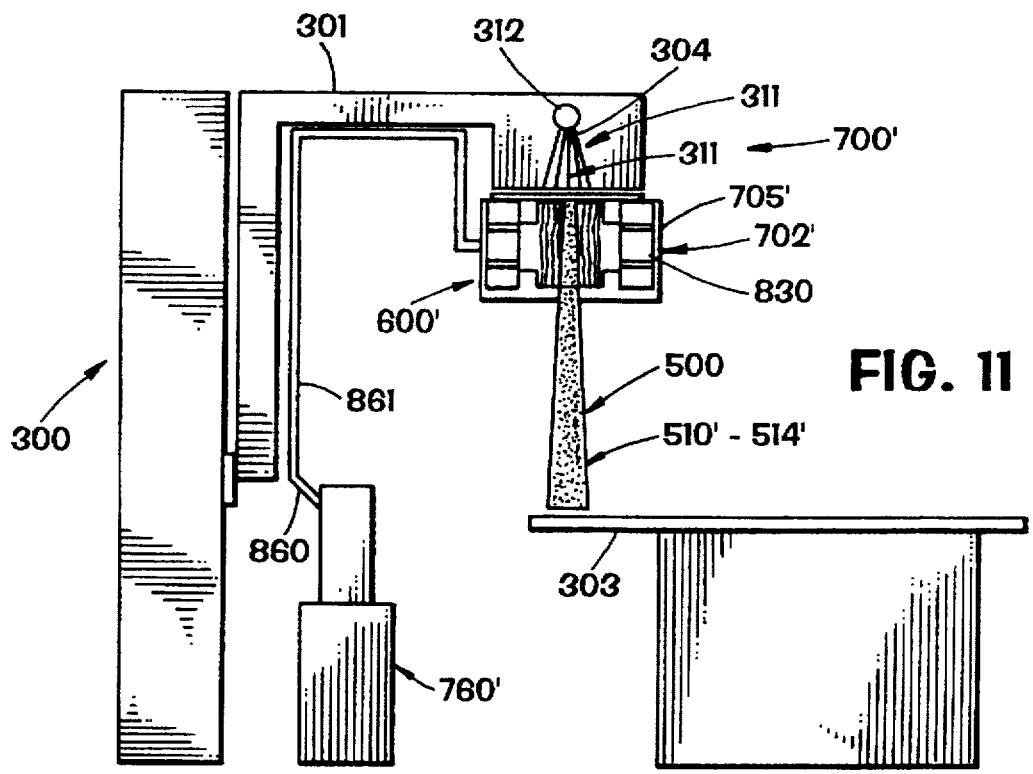
FIG. 11 is a side view of a conventional linear accelerator, provided with the apparatus of FIG. 7.

With reference to FIG. 11, a conventional linear accelerator 300 is shown as including a gantry 301, a patient support table, or patient couch, 303, accelerator head, or beam source, 312, which may include a conventional collimator 304, and a radiation beam 311, having a predetermined, constant beam intensity. The apparatus 700' for use in conformal radiation therapy, is mounted to, and beneath, accelerator head 312, and includes: a means for separating 702' the radiation treatment beam 500 into a plurality of radiation beam segments 510'–514'; and a means for independently modulating 600' the beam intensity of the plurality of radiation beam segments 510'–514' to spatially modulate the beam intensity of the radiation treatment beam 500' across the tumor to be treated. Apparatus 700' includes a control system 760', as will be hereinafter described in greater detail.

With reference to FIGS. 7 and 8, separating means 702' and independent modulation means 600' will be described in greater detail. The means for separating 702' the radiation treatment beam 500' into a plurality of radiation beam segments 510'–514' preferably includes a housing 705', adapted to be secured to the bottom of the accelerator head 312, as shown in FIG. 11. Housing 705' contains a plurality of compartments 820, extending from the top 821 to the bottom 822 of housing 705', sixteen compartments 820 being used for illustration purposes, as shown in FIG. 8. As will be hereinafter described in greater detail in connection with FIGS. 12 and 14, a greater or fewer number of compartments 820 may be provided within housing 705'. Compartments 820, located within housing 705', are generally defined by a plurality of divider members 823 disposed in housing 705'. Preferably, divider members 823 are a plurality of thin dividing rods 824 of any suitable number formed of a stiff radiation non-blocking, or radiolucent, material, such as any suitable radiolucent plastic material, and may be disposed in a staggered relationship as shown in connection with the far left-hand compartment 820.

Figure 12:
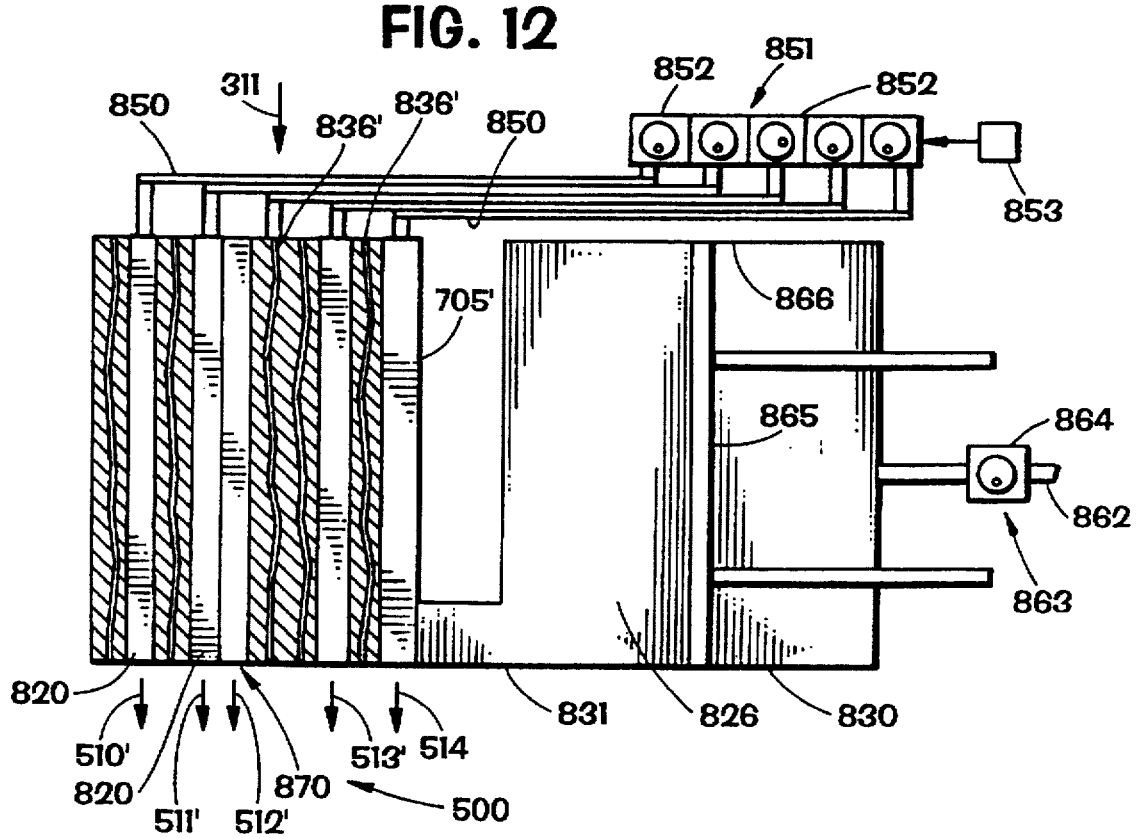
FIG. 12 is a partial cross-sectional, schematic view of the apparatus of FIGS. 7 and 8, wherein some of the expandable, radiolucent members are fully expanded, and some are unexpanded.
Figure 13:
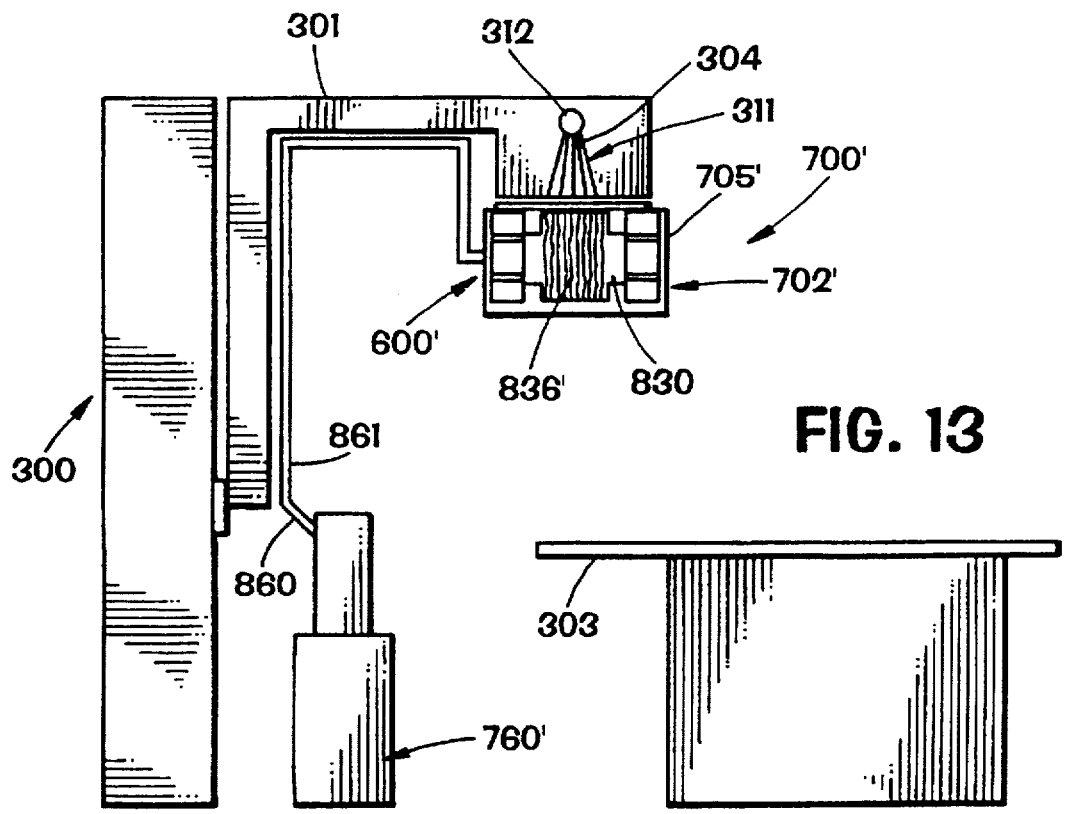
FIG. 13 is a side view of the apparatus of FIG. 11, wherein all of the expandable, radiolucent members of the apparatus of FIG. 7, are unexpanded.
Figure 14:
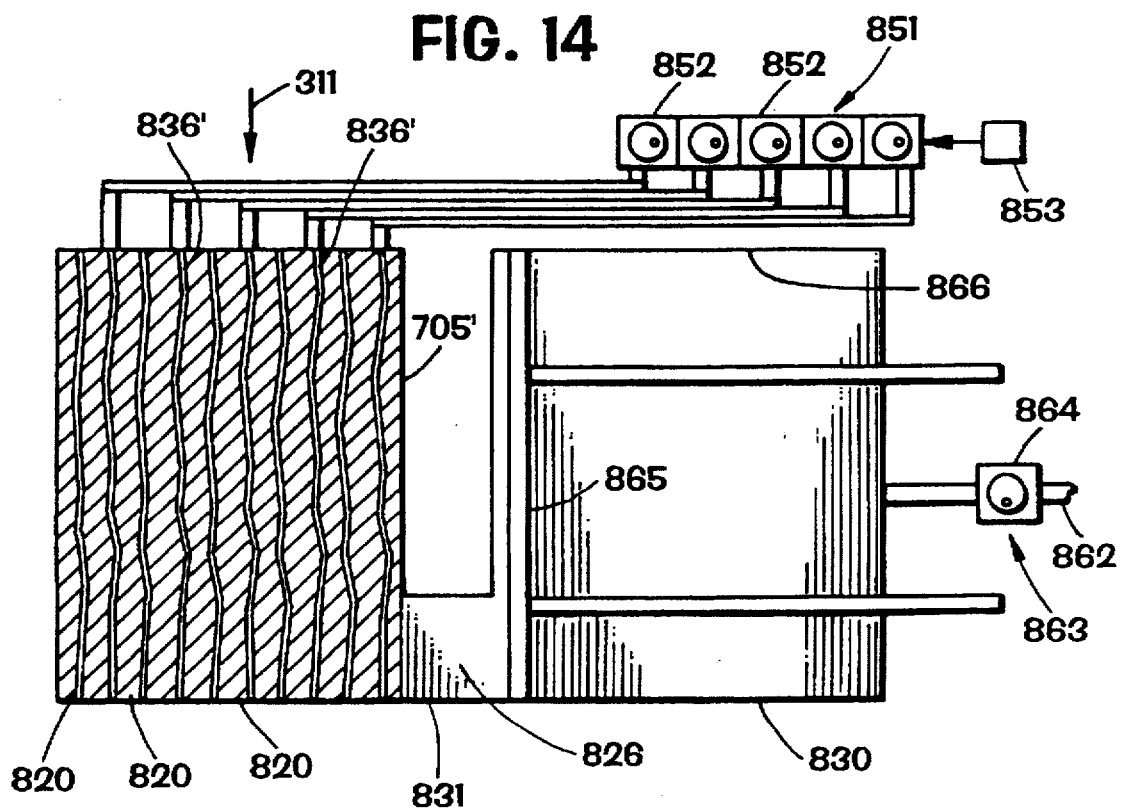
FIG. 14 is a partial cross-sectional, schematic view of the apparatus of FIGS. 7 and 8, wherein all of the expandable, radiolucent members are unexpanded.

With references to FIGS. 7–10, the means for independently modulating 600' the beam intensity of the plurality of radiation beam segments 510'–514' preferably includes a plurality of expandable, radiolucent members 825, and an expandable, radiolucent member 825 is associated with each compartment 820. A quantity of flowable, radiation blocking material 826 (FIGS. 12 and 14) is disposed within housing 705' and within each compartment 820 when the expandable members 825 are unexpanded, as shown in FIGS. 13 and 14. A reservoir 830 for the flowable, radiation blocking material 826 is associated with housing 705', as by providing housing 705' with outlet tubes 831 in fluid communication with the interior 832 of housing 705' and reservoir 830 (FIGS. 12 and 14). Upon expansion of the expandable members 825, the expandable members 825 displace the flowable, radiation blocking material 826 outwardly from the compartment 820 associated with the expandable member 825 and into the reservoir 830 so that a radiation beam segment 510'-514' may pass through the compartments 820 associated with each expanded radiolucent member 825 toward a portion of the tumor 306' (FIG. 4) to be treated.

With reference to FIGS. 7-10, each expandable, radiolucent member 825 is preferably an inflatable balloon 835 formed of a thin radiolucent material, such as latex rubber. Preferably, the thickness of the walls 836 forming inflatable balloons 835 is approximately 0.004–0.006 inches, whereby the inflatable balloons 835 are very flexible. Upon deflation, the walls 836 of inflatable balloons 835 move inwardly toward each other and form what may be considered a non-linear single wall surface 836', having an undulating configuration, as seen in FIGS. 12 and 14. In FIG. 7, four inflatable balloons 835 are illustrated in their expanded, inflated configuration within their associated compartments 820 within housing 705'. Similarly, in FIG. 12, five inflatable balloons 835 are schematically shown in their expanded, inflated configuration within their respective compartments 820 within housing 705'. In FIG. 12, another five expandable, radiolucent members 825, or inflatable balloons 835, are illustrated in their unexpanded, or deflated configuration previously described.

Still with reference to FIGS. 7-10, each inflatable balloon 835 has a substantially square cross-sectional configuration along the longitudinal axis 837 of each balloon 835. In its expanded, inflated configuration, its cross-sectional configuration increases in size from its top 838 to its bottom 839. The bottom portion 839 of each balloon 835 may include a small diameter tubular member 840 adapted to be disposed in fluid communication with a source of pressurized fluid, as will be hereinafter described, in order to selectively inflate, or deflate, each inflatable balloon 835. Similarly, each compartment 820 disposed within housing 705' defined by the plurality of divider members 823 has a substantially square cross-sectional configuration, and the size of the cross-sectional configuration of each compartment 820 diverges, or increases in size, from the top 821 to the bottom 822 of housing 705'. When the expandable member 825, or balloon 835, associated with each compartment is in its expanded, or inflated, configuration, the cross-sectional configuration of each balloon 835 substantially conforms and mates with the cross-sectional configuration of each compartment 820. As is known, the radiation beam 311 entering the housing 705', and originating with the accelerator head 312 (FIG. 11) diverges outwardly as it passes from accelerator head, or beam source, 312, downwardly through housing 705' toward the patient. The degree of the divergence of each compartment 820 is proportional to the divergence of the radiation beam 311 as it travels from accelerator 312, through housing 705' toward the patient on the patient support table 303 (FIG. 11). For a given accelerator head 312, the divergence of the radiation beam 311 is known, whereby the degree of compartment divergence for apparatus 700' can be readily determined. It should be noted that the upper and lower walls 841, 842 of housing 705' are formed of a non-radiation blocking, or radiolucent, material, to permit radiation beam 311 to pass through housing 705'.

As seen in FIG. 8, the lower wall 842 of housing 705' may be provided with a grid of holes, or openings, 843 through which balloons 835 may be disposed within housing 705'. The top 838 of each balloon may be disposed in a spaced relationship from the upper wall 841 of housing 705', as shown in FIG. 7, or alternatively, the top 838 of each balloon 835 may be anchored, or secured, to the underside 845 of the top wall 841 of housing 705', in any suitable manner, such as by glue, a small latex tie, or by wedging the top 838 of each balloon into a small opening formed in the top wall surface 841 of housing 705'. The top 838 of balloon 835 may be formed with an elongated tubular extension, or tip, 838' in which a small plastic ball 838" is placed, the tubular extension 838' and ball 838" being wedged in the top wall surface 841 of housing 705' as illustrated in connection with the far left hand balloon 835 of FIG. 7.

The tubes 840 disposed at the lower end 839 of each balloon 835 pass through an opening 843, in the grid of holes, or openings, 843 in the lower wall 842 of housing 705'. The latex tubes 840 may be rolled upwardly toward the lower wall member 842, as shown at 846, to seal each balloon 835 with respect to the lower wall 842. A seal plate 847 may be secured to the lower wall 842 of housing 705 in an abutting relationship with the rolled ends 846 of tubes 840; the seal plate 847 also being made of a suitable radiolucent material. Seal plate 847 also has a grid of openings, or holes, 848 corresponding to the location of the rolled tube ends 846, and a suitable tubular fitting 849 is threadedly received within each hole 848 and is sealed within the rolled end 846 of each tube 840 of each balloon 835. As seen in FIGS. 12 and 14, each fitting 849 is connected to an air hose 850, and each air hose 850 is connected to a means for selectively inflating, or deflating, 851 each balloon 835. Preferably, the means for selectively inflating, or deflating, 851 each balloon 835 is a solenoid valve 852, and a solenoid valve 852 is associated with each air line 850 associated with each balloon 835. A source of pressurized air 853 provide a pressurized fluid, or pressurized air, to the various solenoid valves 852. As seen in FIG. 7, the upper wall 841 of housing 705' may be provided with tapped mounting holes 854 for securing housing 705' to accelerator head 312, via conventional bolts, or screws (not shown).

With reference to FIGS. 11-14, it is seen that control system 760' has an electric power line 860 extending to the housing 705' to provide electric power for the means for selectively inflating, or deflating, 851 balloons 835, or solenoids 852, as well as an air line 861 to provide the pressurized fluid, or air, to solenoid valves 852. Another air line 862 (FIG. 12) extends from control system 760' to reservoir 830, via a pressure control means 863, or solenoid valve 864, in order to apply a predetermined pressure force upon the radiation blocking material 826 disposed within reservoir 830, as will be hereinafter described. As seen in FIGS. 12 and 14, reservoir 830 may have the form of a piston 865 and cylinder 866 configuration, with pressure control means 863, or solenoid valve 864, supplying a predetermined fluid pressure force upon piston 865.

Preferably, the pressure force on piston 865 is set to a preselected value corresponding to the total weight of the radiation blocking material 826 which is disposed in housing 705', reservoir 830, and connecting tubes 831. Preferably, the predetermined pressure supplied to the means for selectively inflating, or deflating, 851 the balloons 835 is supplied at a higher fluid pressure than the pressure force applied to piston 865. Accordingly, when a preselected balloon 835 is inflated, as shown in FIG. 12, it displaces the flowable, radiation blocking material outwardly from its associated compartment 820 and into reservoir 830 via connector tube 831. Conversely, when a solenoid valve 852, associated with a particular balloon 835, is turned off, the fluid, or air, pressure within a preselected balloon 835 drops, and the pressure force acting upon piston 865 becomes greater than the fluid pressure within the balloon 835. The radiation blocking material 826 then flows from reservoir 830 into the compartment 820 having an unexpanded, deflated balloon 835, whereby the particular compartment 820 is filled with the radiation blocking material 826, and the deflated balloon 835 collapses upon itself as shown at 836'.

When apparatus 700' is in its normal resting state, all of the solenoid valves 852 are turned off, and the fluid pressure surrounding the balloons 835, from the weight of the radiation blocking material 826 and the fluid pressure force upon piston 865, causes all the balloons 835 to collapse, and all of the compartments 820 are filled with the radiation blocking material 826, as illustrated in FIGS. 13 and 14. Since the housing 705' is completely filled with the radiation blocking material 826, radiation beam 311 is not able to pass through housing 705'. FIGS. 11 and 12 illustrate preselected balloons 835 having been inflated, and radiation treatment beam 500, comprised of a plurality of radiation beam segments 510'–514' are able to pass through housing 705' to treat the tumor of the patient.

By selectively filling at least a portion of each of the compartments 820 with the flowable, radiation blocking material 826, or by removing at least a portion of the flowable, radiation blocking material 826 from preselected compartments 820, the beam intensity of the radiation beam segments passing through may be spatially modulated. By controlling the operation of the means for selectively inflating, or deflating, 851, or solenoid valves 852, any arbitrary spatial pattern for modulating the intensities of the individual radiation beam segments may be accomplished. The beam intensity of each radiation beam segment may be modulated to have a predetermined beam intensity, which may be related to the thickness of the portion of the tumor through which the radiation beam passes or the beam intensity may be independent of the thickness of the tumor. Furthermore, the beam intensity may be related to other factors including: the desired dose of radiation to be delivered by the beam segment; the presence, or absence, of sensitive structures, such as healthy tissue or body organs, adjacent the path of each radiation beam segment; and the interaction of other beam segments, and their beam intensities, as they pass through the tumor and healthy tissue and body organs along other beam paths from other directions, in the case of rotational radiation therapy treatments.

It should be noted that although the expandable members, 825, or balloons 835, are formed of a radiolucent material, such as latex rubber, the presence of a deflated balloon 826, as shown at 836' in FIGS. 12 and 14, has little effect on the radiation blocking capacity of apparatus 700' in the region of the collapsed, or deflated, balloon 835, because of the fact that the balloons 835, when deflated, deform in a non-linear fashion, and have the undulating configurations illustrated in FIGS. 12 and 14.

Temporal modulation of the beam intensities of each radiation beam segment 510'–514' of radiation treatment beam 500 may be accomplished by varying the amount of time each compartment 820 is selectively filled with the flowable, radiation blocking material 826. The beam intensity of each radiation beam segment may be modulated, or attenuated, by completely filling a preselected compartment 820 with radiation blocking material 826, as by completely deflating a preselected balloon 835. The size of the treatment field for radiation treatment beam 500 is determined by the size and number of compartments 820 provided in housing 705', whereby the greater number of compartments 820 provided, results in a larger treatment field. In many instances, it is believed that, dependent upon the number of compartments 820 provided, the treatment field will be of a sufficient size to encompass a volume of tissue 400 (FIGS. 3D and FIG. 5), which volume of tissue 400 contains the entire tumor 306' to be treated. However, because in the checkerboard embodiments only half of the tumor volume may be exposed to radiation at one time, two rotations of the gantry 301 of linear accelerator 300 may be necessary to provide the desired treatment to tumor 306' for a given orientation of the patient with respect to the apparatus 700', before the orientation of the tumor 306' with respect to accelerator head 312 is changed, as by rotating patient support table 303, as previously described in connection with FIG. 1.

When using apparatus 700', a static radiation treatment field can be created by maintaining a preselected number of compartments 820 filled with radiation blocking material 826, while the remaining preselected compartments are devoid of radiation blocking material 826, as illustrated in FIG. 12. Such a static radiation treatment field has distinct advantages over conventional multileaf collimator static radiation treatment fields, because "islands" of radiation blocking material, such as island 870 in FIG. 12 formed by radiation beam segments 511' and 512' can be disposed within the radiation treatment field. Such "islands" are not possible with conventional multileaf collimators, since they only "shape" or conform the outer edges of a radiation treatment beam. Rotational radiation therapy treatments may be provided with apparatus 700', whereby as the accelerator gantry 301 rotates about the patient, control system 760' controls the operation of the means for selectively inflating, or deflating, 851 balloons 835. Control system 760' provides the necessary and appropriate control signals to apparatus 700' in the manner previously described in connection with FIG. 6.

With reference to FIGS. 15–21, the method and apparatus 700" for conformal radiation therapy of the present invention will be described. While the previously described method and apparatus 700' for conformal radiation therapy, as described in connection with FIGS. 7–14 is believed to be effective in spatially and temporally modulating a linear accelerator beam, the dosimetry involved in creating treatment plans and the construction of the housing 705' could be quite complex. For example, construction of the housing 705' requires thin dividing rods 824 made of suitable radiolucent plastic material, which may be disposed in a staggered relationship as shown in connection with the far left-hand compartment 820, thereby forming a grid pattern into which the balloons are introduced. The method and apparatus 700" of the present invention reduces the dosimetric calculations required and reduces the complexity of construction of housing 705'.

The apparatus 700" for use in conformal radiation therapy, in accordance with the present invention, may be mounted to, and beneath, accelerator head 312 (shown in FIG. 11), and includes: a means for separating 702" the radiation treatment beam 500 into a plurality of radiation beam segments 510–514, 510'–514' (FIG. 5); and a means for independently modulating 600" the beam intensity of the plurality of radiation beam segments 510–514, 510'–514' (FIG. 5) to spatially modulate the beam intensity of the radiation treatment beam 500 across the tumor to be treated. Apparatus 700" includes a control system 760", as will be hereinafter described in greater detail. Components denoted with primed referenced number have generally the same function and/or similar structure to components denoted with unprimed reference numbers previously described.

Figure 15:
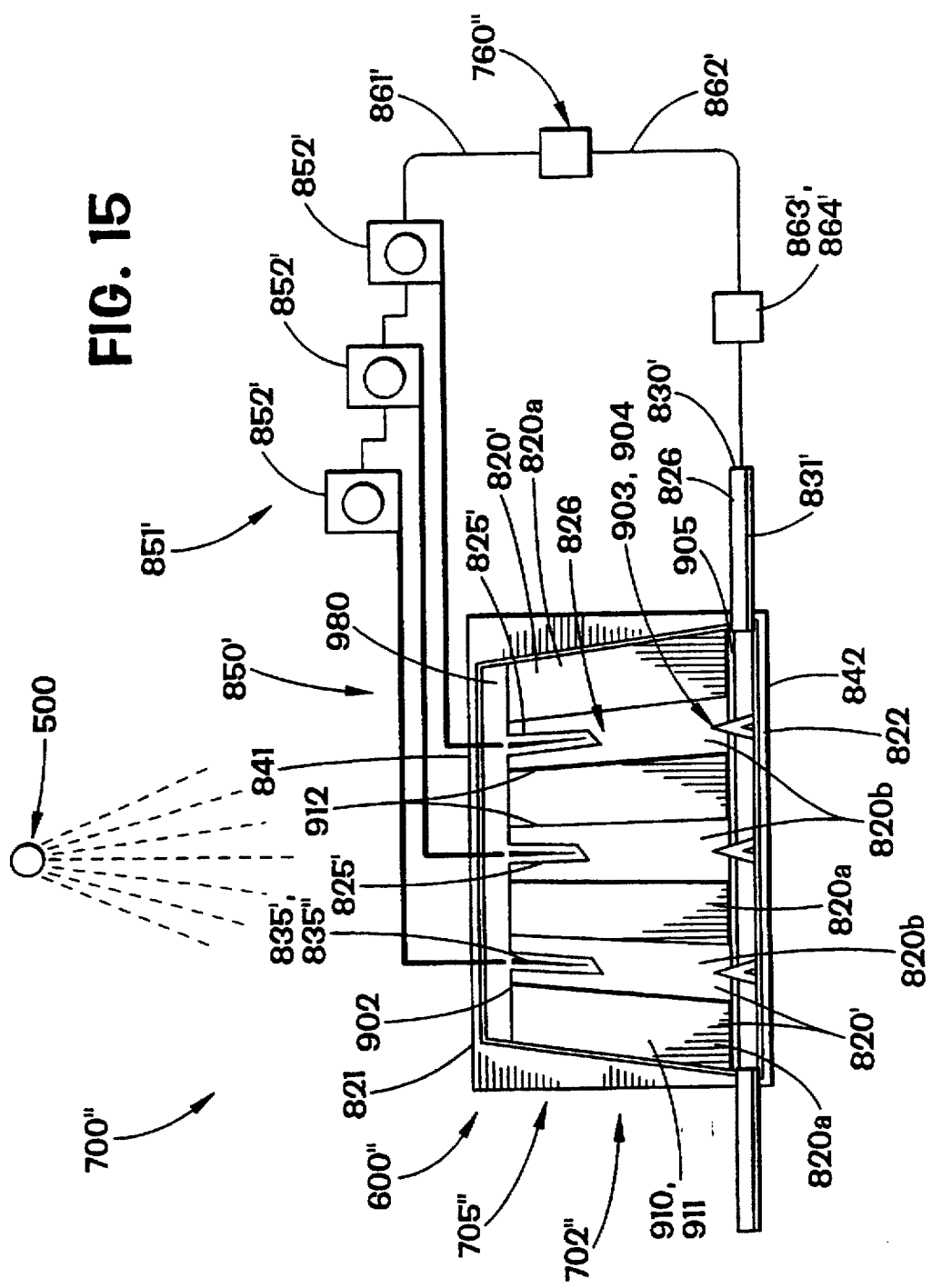
FIG. 15 is a partial cross-sectional schematic view of an embodiment of the apparatus of the present invention showing an array of solid, radiopaque blocking members.

With reference to FIGS. 15–21, separating means 702" and independent modulation means 600" will be described in greater detail. The means for separating 702" the radiation treatment beam 500 into a plurality of radiation beam segments 510–514, 510'–514' (FIG. 5) preferably includes a housing 705", adapted to be secured to the bottom of the accelerator head 312 (FIG. 11). Housing 705" contains a plurality of compartments 820', extending from the top 821 to the bottom 822 of housing 705". FIG. 15 shows seven compartments 820'. As will be hereinafter described in greater detail in connection with FIGS. 18–21, the compartments 820' are arranged in a checkerboard array 900, and greater or fewer of compartments 820' may be provided within housing 705". The checkerboard array 900 is generally defined by alternating closed compartments 820a and radiolucent, or open, compartments 820b, located within a housing 705". Preferably, closed compartments 820a are a plurality of blocks 910 of rigid radiation blocking material, such as tungsten, or any suitable radiopaque material. However, the closed compartments 820a may also be a plurality of hollow containers 911, which are comprised of rigid radiation blocking walls. Moreover, unless otherwise specified, the term block is intended to mean any rigid radiation blocking construction, whether solid or otherwise. The dimensions of the blocks 910, or containers 911, may be chosen such that the blocks 910, or containers 911, fully extend from the top 821 to the bottom 822 of the housing 705". Radiolucent, or open, compartments 820b are defined by the walls 912 of blocks 910 or containers 911. The compartments 820 are configured so that their cross-sectional area is greater at the bottom 822 of the housing 705" than at the top 821 of the housing 705", thereby creating a divergence of the radiolucent, or open, compartments 820b proportional to the divergence of the radiation beam 500.

Figure 16:
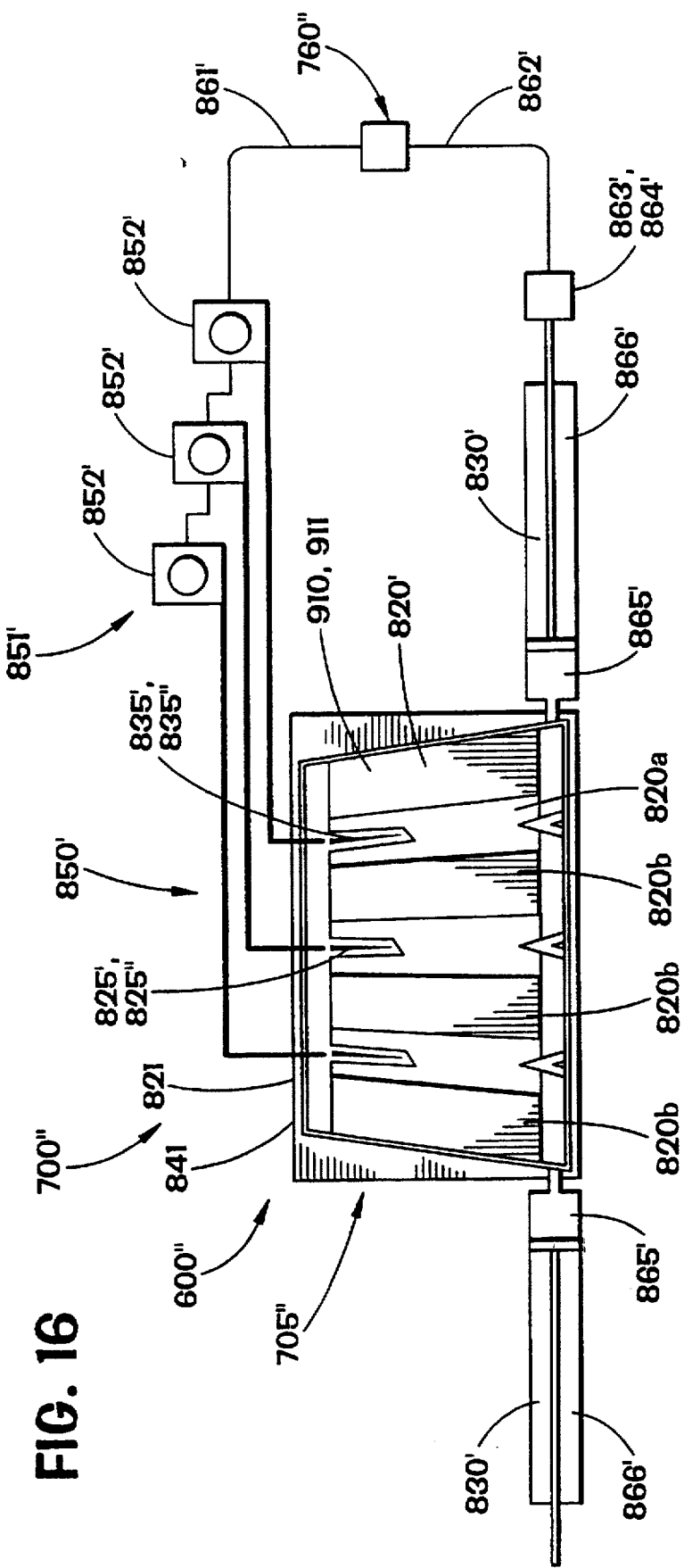
FIG. 16 is a partial cross-sectional view of the apparatus of an embodiment of the present invention showing an array of radiopaque blocking members wherein the expandable radiolucent members are unexpanded.
Figure 17:
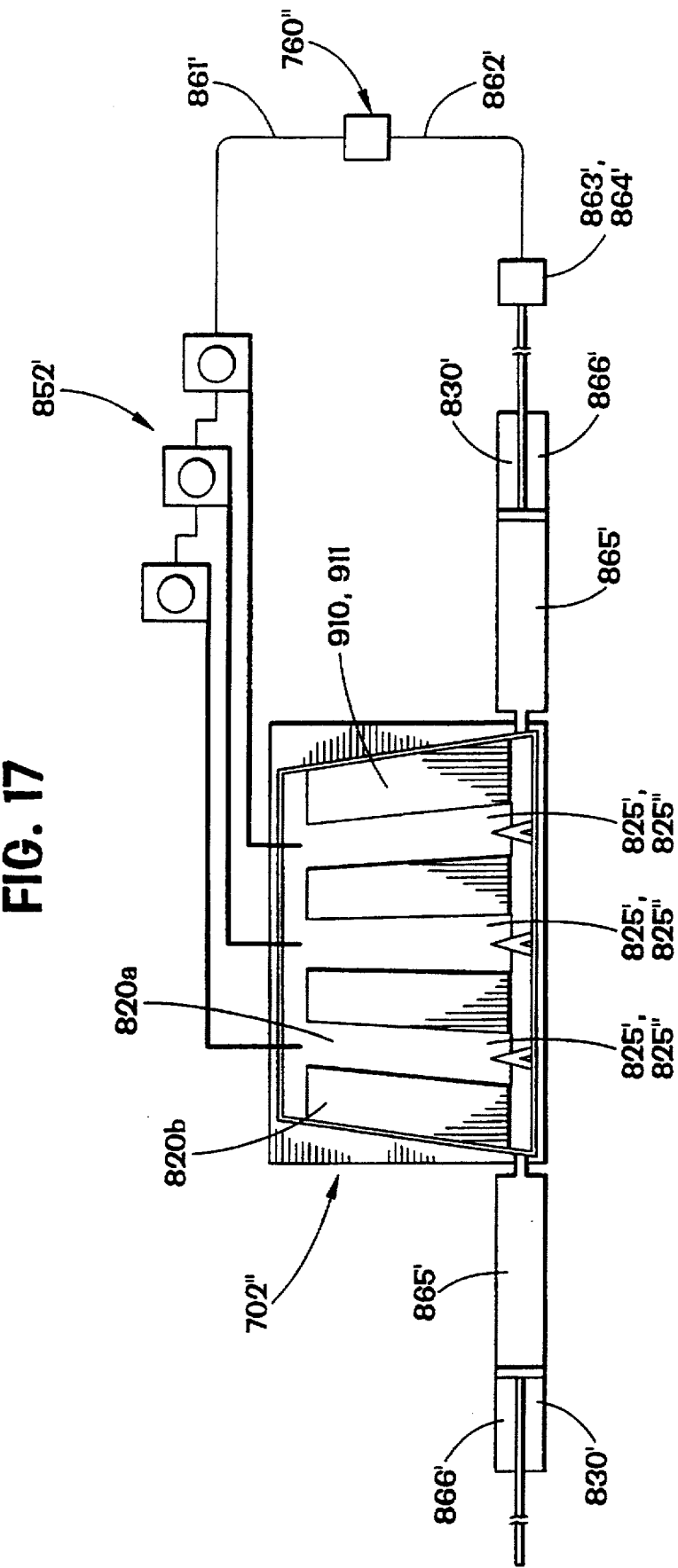
FIG. 17 is a partial cross-sectional view of the apparatus of an embodiment of the present invention showing an array of radiopaque blocking members wherein the expandable radiolucent members are expanded.
Figure 22:
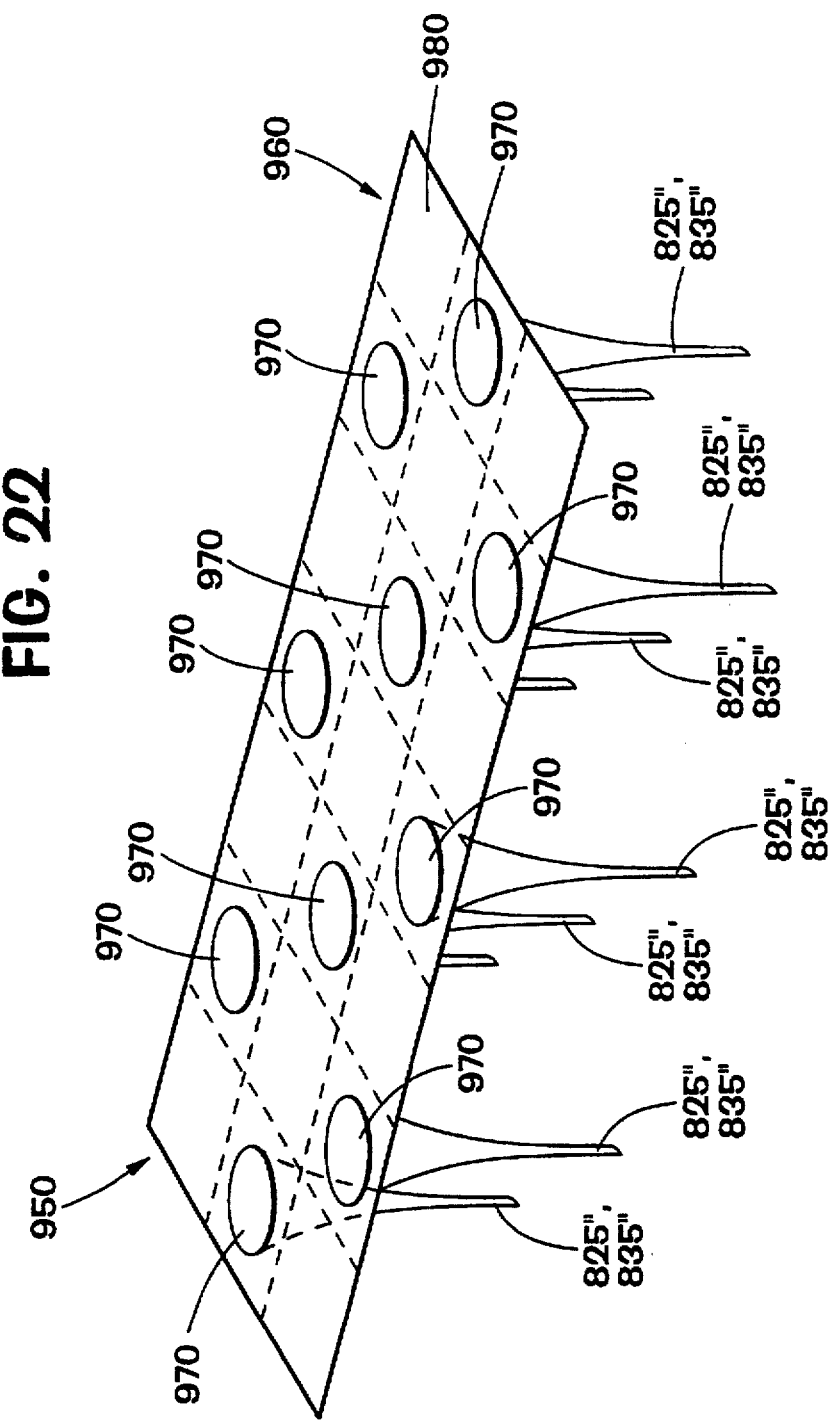
FIG. 22 is a perspective view of a balloon array of the present invention.

With references to FIGS. 15–17 and 22, the means for independently modulating 600" the beam intensity of the plurality of radiation beam segments 510'–514', preferably includes a plurality of expandable, radiolucent members 825', 825", and an expandable, radiolucent member 825', 825", is associated with each radiolucent, or open, compartment 820b. The plurality of radiolucent members 825', 825", may be integrally formed in a balloon array 950 (FIG. 22) or may be individual balloons 835' (FIG. 9). FIG. 22 shows a plurality of radiolucent members 825" formed integrally in a balloon array 950. It should be noted that where the radiolucent members 825" are formed integrally in a balloon array 950 (FIG. 22) the individual balloons 835" may not have the tubular member 840, which may be included in the individual balloons 835, 835' that are attached separately to their respective compartments. The balloon array 950 may preferably be formed of latex but any other suitable radiopaque material may be used. The balloon array 950 may resemble a glove, whereby the radiolucent members 825' protrude from a grid layer 960 as fingers protrude from a glove. However, where the body of a glove is shaped to conform to a hand, the grid layer 960 is shaped to conform to the top 821 of the housing 700" (FIGS. 15–17).

Preferably, the top 821 of the housing 700" is planar such that the grid layer 825b' is also planar. However, the top 821 and the grid layer 960 may be of any shape consistent with the application of the present invention.

The balloons 835" protrude from the grid layer 960, creating openings 970 in the surface, or membrane 980, of grid layer 960. The openings 970 and protruding balloons 835" are preferably spaced-apart to conform to the checkerboard array 900 (FIGS. 18–21) of the housing 700". However, the array 950 of protruding balloons 835" may also be spaced-apart to conform to the spacing of compartments 820 of housing 700' (FIGS. 7, 8, 11–14). Where the openings 970 and protruding balloons 835" are spaced-apart to conform to the checkerboard array 900 of the housing 700", each opening 970 corresponds to the location of a radiolucent, or open, compartment 820b in such a way that each finger, or balloon 835', 835" can extend into a radiolucent, or open, compartment 820b. When the balloons 835', 835" are expanded, the balloon can conform to the shape of the radiolucent, or open, compartment 820b, thus forcing out the radiation blocking material 826. A quantity of flowable, radiation blocking material 826 is disposed within housing 705" and within each radiolucent, or open, compartment 820b when the expandable members 825', 825" are unexpanded, as shown in FIGS. 15 and 16. A reservoir, or reservoirs, 830' (FIGS. 16–17) for the flowable, radiation blocking material 826 is associated with housing 705", as by providing housing 705" with outlet tube, or tubes 831 ' in fluid communication with the interior 832' of housing 705" and the reservoirs 830' (FIGS. 16–17). Upon expansion of the expandable members 825', 825" the expandable members 825', 825" displace the flowable, radiation blocking material 826 outwardly from the radiolucent, or open, compartment 820b associated with the expandable member 825', 825" and into the reservoirs 830' (FIGS. 16–17) so that a radiation beam segment 510–514, 510'–514' may pass through the radiolucent, or open, compartments 820b associated with each expanded radiolucent member 825', 825" toward a portion of the tumor 306' (FIG. 4) to be treated.

With reference to FIGS. 15–17, each expandable, radiolucent member 825' is preferably an inflatable balloon 835' or an array 950 of inflatable balloons 835", formed of a thin radiolucent material, such as latex rubber. Preferably, the expandable, radiolucent members 825', 825" are inflatable balloons 835" formed integrally with a membrane 980, forming an array 950 of radiolucent members 825" in a pattern corresponding to the pattern of the checkerboard array 900. Upon deflation, the walls of inflatable balloons 835" move inwardly toward each other and form what may be considered a non-linear single wall surface 836' (FIGS. 9–10), having an undulating configuration. In FIG. 17, three expandable, radiolucent members 825', 825", inflatable balloons 835', 835" are illustrated in their expanded, inflated configuration within their associated radiolucent, or open, compartments 820b within housing 705". In FIGS. 15–17, the same three expandable, radiolucent members 825', 825" or inflatable balloons 835', 835" are illustrated in their unexpanded, or deflated configuration previously described.

Still with reference to FIGS. 15–17 and FIGS. 9–10, each inflatable balloon 835', 835" has a substantially square cross-sectional configuration along the longitudinal axis 837' of each balloon 835', 835". Each radiolucent, or open, compartment 820b disposed within housing 705" defined by the blocks 820a has a substantially square cross-sectional configuration, and the size of the cross-sectional configuration of each radiolucent, or open, compartment 820b diverges, or increases in size, from the top 821 to the bottom 822 of housing 705". When the expandable member 825', 825" or balloon 835', 835" associated with each compartment is in its expanded, or inflated, configuration, the cross-sectional configuration of each balloon 835', 835" substantially conforms and mates with the cross-sectional configuration of each radiolucent, or open, compartment 820b. As is known, the radiation beam 311 (FIG. 11) entering the housing 705", and originating with the accelerator head 312 (FIG. 11) diverges outwardly as it passes from accelerator head, or beam source, 312 (FIG. 11), downwardly through housing 705" toward the patient. The degree of the divergence of each radiolucent, or open, compartment 820b is proportional to the divergence of the radiation beam 311 (FIG. 11) as it travels from accelerator 312 (FIG. 11), through housing 705" toward the patient on the patient support table 303 (FIG. 11). For a given accelerator head 312 (FIG. 11), the divergence of the radiation beam 311 (FIG. 11) is known, whereby the degree of compartment divergence for apparatus 700' (FIG. 11) can be readily determined. It should be noted that the upper and lower walls 841, 842 of housing 705" are formed of a non-radiation blocking, or radiolucent, material, to permit radiation beam 311 (FIG. 11) to pass through housing 705".

Figure 19:
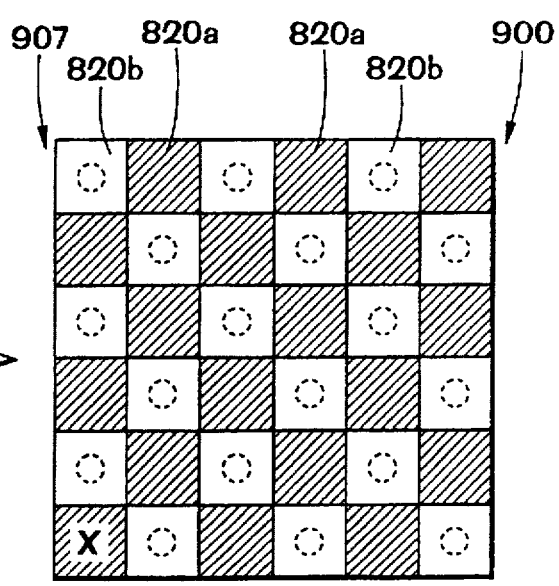
FIG. 19 is a cross-sectional view of an embodiment of the apparatus of the present invention, showing a square array in a second position, rotated 90° in a counter-clockwise direction.

As shown in FIG. 15–17, the upper wall 841 of housing 705' may be provided with a grid of openings 843' through which balloons 835', 835" may be disposed within housing 705". In its deflated state, the bottom 838' of each balloon 835', 835" may be disposed in a spaced relationship from the lower wall 842 of housing 705", as shown in FIG. 19. As shown in FIG. 17, when inflated, the bottom 838' of each inflated balloon 835', 835" may contact the lower wall 841 of housing 705, thus completely filling the radiolucent, or open, compartment 820b.

Preferably, the means for selectively inflating, or deflating, 851' each balloon 835', 835" is a solenoid valve 852', and a solenoid valve 852' is associated with each air line 850' associated with each balloon 835', 835". A source of pressurized air (not shown) provides a pressurized fluid, or pressurized air, to the various solenoid valves 852'.

With reference to FIGS. 15–17, it is shown that control system 760" has an air line 861' to provide the pressurized fluid, or air, to solenoid valves 852'. Another air line 862' extends from control system 760" to reservoir 830', via a pressure control means 863', or solenoid valve 864', in order to apply a predetermined pressure force upon the radiation blocking material 826 disposed within reservoir 830', as will be hereinafter described. As seen in FIGS. 16 and 17, reservoir 830' may have the form of a piston 865' and cylinder 866' configuration, with pressure control means 863' (FIG. 15), or solenoid valve 864' (FIG. 15), supplying a predetermined fluid pressure force upon piston 865'. When a preselected balloon 835', 835" is inflated, as shown in FIG. 17, it displaces the flowable, radiation blocking material outwardly from its associated radiolucent, or open, compartment 820b and into reservoir 830' via connector tube 831'. When a solenoid valve 852', associated with a particular balloon 835', 835", is turned off, the pressure force acting upon piston 865' becomes greater than the fluid pressure within the balloon 835', 835". The radiation blocking material 826 then flows from reservoir 830' into the radiolucent, or open, compartment 820b having an unexpanded, deflated balloon 835', 835", whereby the particular radiolucent, or open, compartment 820b is filled with the radiation blocking material 826, and the deflated balloon 835', 835" collapses. When apparatus 700" is in its normal resting state, all of the solenoid valves 852' are turned off, and the fluid pressure surrounding the balloons 835', 835", from the weight of the radiation blocking material 826 and the fluid pressure force upon piston 865', causes all the balloons 835', 835" to collapse, and all of the radiolucent, or open, compartments 820b are filled with the radiation blocking material 826, as illustrated in FIGS. 15 and 16. Since the housing 705" is completely filled with the radiation blocking material 826, radiation beam 311 (FIG. 11) is not able to pass through housing 705".

Because the radiolucent, or open, compartment 820b of housing 705" is defined by the solid walls of blocks 910, or containers 911, it may not be necessary that the balloons be attached to the lower wall 842 of housing 705". As shown in FIGS. 15–17, the apparatus 700" of the present invention may also include a sensing mechanism 903, including electrical contacts, or inflation sensors, 984, which may communicate with control system 760" to shut off power to the linear accelerator 300 (FIG. 11) in the event of failure of a balloon 835'. To retain the balloons 835' within the radiolucent, or open, compartment 820b when expanded, a screen 905 may be provided proximate the lower wall 842 of the housing 705".

By selectively filling at least a portion of each of the radiolucent, or open, compartments 820b with the flowable, radiation blocking material 826, or by removing at least a portion of the flowable, radiation blocking material 826 from preselected radiolucent, or open, compartments 820b, the beam intensity of the radiation beam segments passing through may be spatially modulated. By controlling the operation of the means for selectively inflating, or deflating, 851', or solenoid valves 852', any arbitrary spatial pattern for modulating the intensities of the individual radiation beam segments may be accomplished. The beam intensity of each radiation beam segment may be modulated to have a beam intensity related to the thickness of the portion of the tumor through which the radiation beam passes or the beam intensity may be independent of the thickness of the tumor. Furthermore, the beam intensity may be related to other factors including: the desired dose of radiation to be delivered by the beam segment; the presence, or absence, of sensitive structures, such as healthy tissue or body organs, adjacent the path of each radiation beam segment; and the interaction of other beam segments, and their beam intensities, as they pass through the tumor and healthy tissue and body organs along other beam paths from other directions, in the case of rotational radiation therapy treatments.

Figure 18:
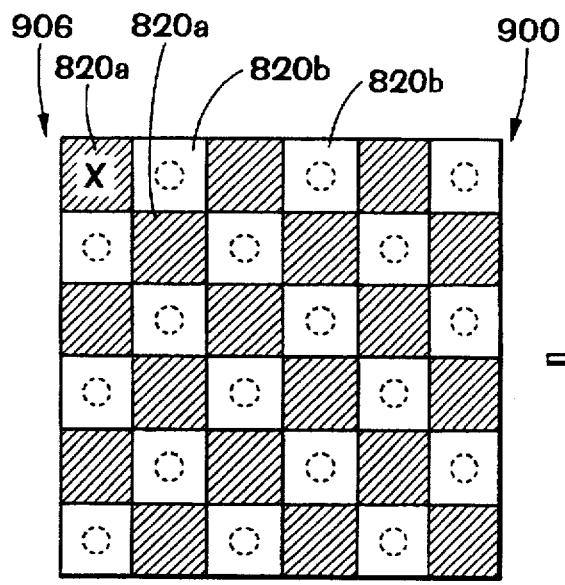
FIG. 18 is a cross-sectional view of an embodiment of the apparatus of the present invention, showing a square array of radiolucent, or open, compartments and closed compartments in a first position.
Figure 20:
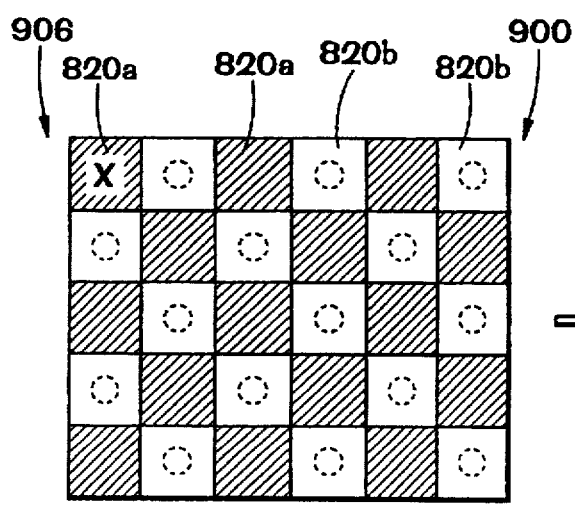
FIG. 20 is a cross-sectional view of an embodiment of the apparatus of the present invention, showing a rectangular array in a first position.
Figure 21:
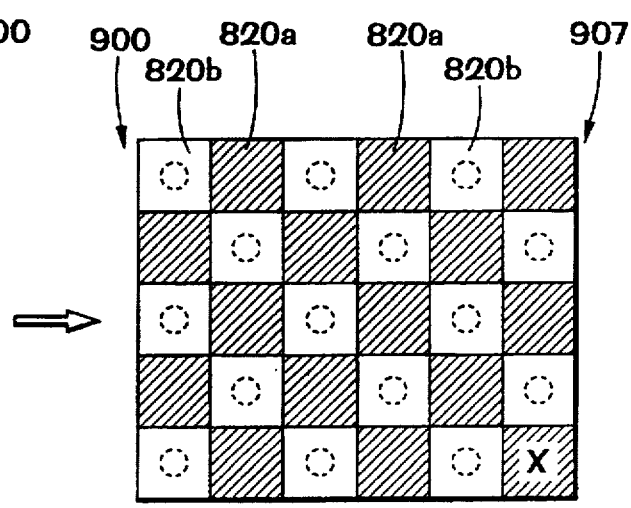
FIG. 21 is a cross-sectional view of an embodiment of the apparatus of the present invention, showing a rectangular array in a second position rotated 180°.

As shown in FIGS. 22–25, the compartments 820' are arranged in a checkerboard array 900. The checkerboard array 900 is generally defined by alternating closed compartments 820a and radiolucent, or open, compartments 820b, located within housing 705". The array 900 may be either square (as shown in FIG. 18), having an equal number of compartments 820' on each side, or the array 900 may be a rectangle, having a greater number of compartments 820' on one side. In any event, the array 900 should include at least nine compartments 820' in a 3×3 configuration. FIGS. 18 and 19 show a 6×6, square, configuration. However, a greater or lesser number of compartments 820' may be utilized. For example, FIGS. 20 and 21 show a 6×5, rectangular, configuration.

Where beam 311 is introduced to the array 900 in a first position 906 (FIGS. 18 and 20), the radiolucent, or open, compartments 820b only allow half of the tumor volume to be exposed to radiation. In order to expose the other half of the volume, the array 900 is either rotated or indexed to a second position 907 (FIGS. 19 and 21), as described hereafter in further detail. Where the array 900 has a square configuration, with an even number of compartments 820' per side, the array 900 may be rotated 90 degrees from its first position 906 to its second position 907 to expose the remaining tumor volume. Where the array 900 has a rectangular configuration (as shown in FIGS. 20–21), the array 900 may be rotated 180 degrees from its first position 906 to its second position 907 to expose the remaining tumor volume. Where the array 900 has a square configuration (as shown in FIGS. 18–21), with an odd number of compartments 820' per side, the array 900 must be indexed, or shifted, the width of one compartment 820' to expose the remaining tumor volume. Where the array 900 is indexed, or shifted, the indexing mechanism (not shown) must index, or shift, the array 900 along an arc (not shown) consistent with the divergent nature of the radiation beam 311 (FIG. 11). In its first position, the closed compartments 820a of radiation blocking material blocks half of the tumor volume from radiation. The indexing or rotating of the array 900 exposes the remaining half of the tumor volume because the portions of the tumor volume that were previously treated will be blocked from radiation by a closed compartment 820a and the portions of the tumor volume that were previously blocked from radiation by a closed compartment 820a will now be exposed through a radiolucent, or open, compartment 820b.

Temporal modulation of the beam intensities of each radiation beam segment 510–514, 510'–514' of radiation treatment beam 500 (FIG. 11) may be accomplished by varying the amount of time each compartment 820' is selectively filled with the flowable, radiation blocking material 826. The beam intensity of each radiation beam segment may be modulated, or attenuated, by completely filling a preselected compartment 820' with radiation blocking material 826, as by completely deflating a preselected balloon 835'. The size of the treatment field for radiation treatment beam 500 (FIG. 11) is determined by the size and number of compartments 820' provided in housing 705', whereby the greater number of compartments 820' provided, results in a larger treatment field. In many instances, it is believed that, dependent upon the number of compartments 820' provided, the treatment field will be of a sufficient size to encompass a volume of tissue 400 (FIGS. 3D and FIG. 5), which volume of tissue 400 contains the entire tumor 306' to be treated. Thus, only one rotation of the gantry 301 of linear accelerator 300 will be necessary to provide the desired treatment to tumor 306' for a given orientation of the patient with respect to the apparatus 700", before the orientation of the tumor 306' with respect to accelerator head 312 is changed, as by rotating patient support table 303, as previously described in connection with FIG. 1.

When using apparatus 700", a static radiation treatment field can be created by maintaining a preselected number of compartments 820b' filled with radiation blocking material 826, while the remaining preselected compartments are devoid of radiation blocking material 826, similar to that as illustrated in FIG. 16. Such a static radiation treatment field has distinct advantages over conventional multileaf collimator static radiation treatment fields, because "islands" of radiation blocking material, such as island 870 in FIG. 16 formed by radiation beam segments 511' and 512' can be disposed within the radiation treatment field. Such "islands" are not possible with conventional multileaf collimators, since they only "shape" or conform the outer edges of a radiation treatment beam. Rotational radiation therapy treatments may be provided with apparatus 700", whereby as the accelerator gantry 301 rotates about the patient, control system 760" controls the operation of the means for selectively inflating, or deflating, 851' balloons 835'. Control system 760" provides the necessary and appropriate control signals to apparatus 700" in a manner hereinafter described in connection with FIG. 10.

Figure 6:
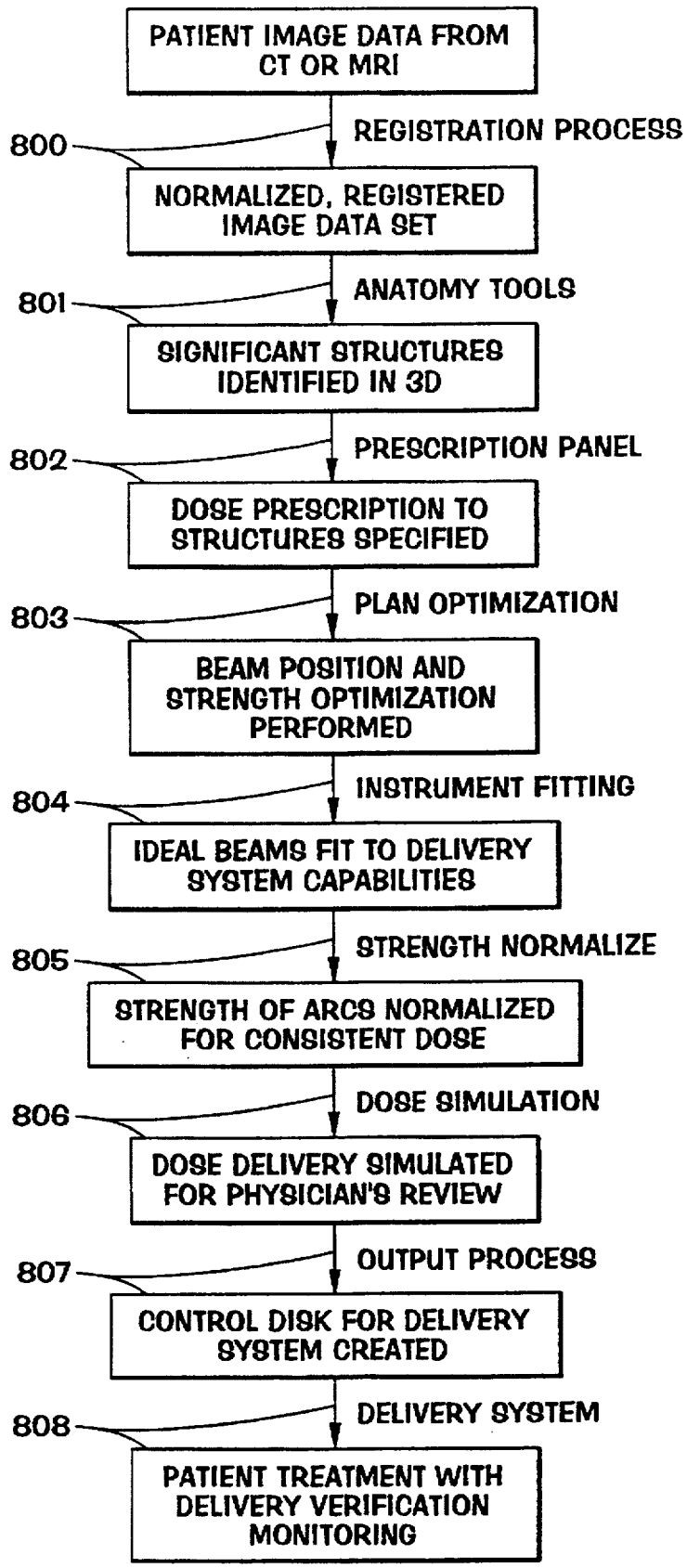
FIG. 6 is a flow diagram of a radiation planning system for controlling the operation of the apparatus of the present invention.

In order for apparatus 700" or the method of conformal radiation therapy of the present invention to efficiently operate it is necessary that appropriate control signals be provided to the electronics 760" of apparatus 700" to control the operation of apparatus 700", including the means for independently modulating 600" the beam intensity of the radiation beam segments of the radiation treatment beam used in apparatus 700". For example, dependent upon the location, size, and dimensions of a particular tumor within a patient's body, it is necessary to determine the dose of radiation to be directed toward the tumor portions disposed within the various slice-shaped portions of tissue volume being treated, with respect to the radial position of the radiation beam source used to treat the particular slice-shaped portions of tissue. Conventional radiation planning system are available which can provide the necessary control information utilized to control apparatus 700" and permit the method of conformal radiation therapy of the present invention to be performed. With reference to FIG. 6, a preferred radiation planning system to obtain the information that is utilized by apparatus 700" and in practicing the method of the present invention will be described.

The first step of the process is generally referred to as the Registration Process step 800. This is the process step of aligning a set of conventional axial slice images of the portion of the patient to be treated by the conformal radiation therapy of the present invention. These images are first obtained by conventional computerized tomographic ("CT") scanning or magnetic resonance imaging ("MRI") techniques which produce an image representing a "slice" of tissue displayed with anatomical accuracy. The series of "slices", which constitute the complete CT or MRI study, represents a three-dimensional picture of a particular portion of the patient, to allow visualization as a valid three-dimensional data set. The resulting data is achieved by sampling the input data, determining common marks of known geometry, and warping the data to be correctly aligned. Resulting resolution is set so that it is geometrically correct based on the known patient fixation device utilized, as previously described, and if images have been scanned from film, gray scale image normalization is done based on reference graybars including in the images. Conventional two-dimensional image warping techniques are utilized, with super sampling and filtering as required for resolution adjustment. Image slice spacing is entered by the operator of the planning system and verified by the known patient fixation device geometry.

The next step of the system is generally referred to as the Anatomy Tools step 801. The physician identifies the three-dimensional volume of the structure significant to radiation planning, in a conventional manner, whereby the physician identifies anatomical structures on an image slice-by-slice basis.

The Prescription Panel step 802 allows the physician to input into the planning system the desired goal of the radiation therapy treatment, in terms of the desired target dose, sensitive structure limits, delivery complexity, and aggressiveness. Aggressiveness relates to the relative importance of maximally treating the target, or tumor, as compared with sparing sensitive, adjacent anatomical structures. These parameters are utilized in the plan optimization step 803.

In the Plan Optimization step 803, the radiation plan optimization is a specific case of an inverse problem, where the goal is to determine the best way to achieve the dose prescription. A Simulated Annealing technique is utilized to do this optimization by dividing the radiation delivery into a series of narrow slices, or slice-shaped portions, or arc treatments, and optimizing each of these arcs separately. The annealing cooling schedule utilized, fits into the class of FSA (Fast Simulated Annealing) techniques. The details of the foregoing simulated annealing techniques are known in the art and are described in such publications as "Optimization of Conformal Radiotherapy Dose Distributions by Simulated Annealing", S. Webb, Physics and Medical Biology, Vol. 34, PP. 1349–1370 (1989); and "Optimization of Conformal Radiotherapy Dose Distributions by Simulated Annealing: 2. Inclusion of Scatter in the 2d Technique", S. Webb, Physics and Medical Biology, vol. 36, pp. 1227–1237, (1991), which publications are incorporated herein by reference. A suitable computer is utilized in performing the Plan Optimization step, as well as the other steps of the radiation planning system.

The next step in the planning system is the Instrument Fitting step 804. The resulting optimized set of radiation beam positions and beam weights, or beam intensities for the radiation beam segments, is fitted into the delivery capabilities of apparatus 700', 700", after optimization. An iterative process is utilized to account for OF adjustments (Output Factor), the timing of the movement of members, and limitations of simultaneous movements to arrive at control information for apparatus 700" that represent the optimized plan and can be delivered within the operating limitations of device 700".

A Strength Normalize step 805 further normalizes the arcs of rotation through which the radiation beam source travels to insure that the tumor receives a consistent radiation dose from each position selected in order to eliminate what are known as "hot" or "cold" regions in the tissue volume being treated. This step may be done by varying the radiation dose rate of the radiation source, and may be accomplished by use of a conventional, simple linear scaling technique.

In the Dose Simulation step 806 the radiation dose to the patient is simulated based upon the control information for device 700". The algorithm used in this step is based upon the Three-Dimensional Modified Path Length technique, as is known in the art. Examples of this algorithm are discussed in the following publications: "Algorithm for Dosimetry of Multiarc Linear Accelerator Stereotactic Radiosurgery", G. Luxton et al., Medical Physics, vol. 18, pp. 1211–1221 (1991); "Dosage Calculations in Radiation Therapy", W. L. Saylor, published by Urban & Schwarzenberg (1979), which publications are incorporated herein by reference.

The Output Process step 807 permits the physician to review the simulated radiation dose information and to approve the radiation plan for patient delivery. After such review and approval, a floppy disk is generated containing the data to control apparatus 700" for the specific radiation delivery case. The data includes instructions for the timing and movement of members, radiation source setup information, and conventional patient information. After the foregoing steps have been accomplished, the Delivery System step 808 is accomplished, wherein the method steps of the conformal radiation therapy method of the present invention are performed as previously described, in order to treat the tumor in the patient.

The method and apparatus 700" may be utilized in rotational radiation therapy plans, wherein it is preferred that no more than 10 non-coplanar arcs of approximately 210 degrees are used, although any number of arcs may be used, if desired, which arcs may vary from 0 degrees to 360 degrees. The positioning and location of the arcs with respect to the patient, and the number of arcs utilized are determined in accordance with the previously described planning system. Preferably, the beam intensities of the radiation beam segments directed toward the tumor are updated every 5 degrees of rotation, whereby an optimized dose distribution for the tumor will be produced. However, other degrees of rotation may be specified. Conventional fixed port radiation treatment plans can also be practiced with apparatus 700" of the present invention. The ports do not have to be coplanar, and the location of the ports can be either inputted into apparatus 700" by the physician, or optimized by the radiation planning system previously described. The foregoing rotational radiation treatment plan, or fixed port radiation plan can be used for tumors occurring anywhere in the body with the method and apparatus of the present invention.

It is to be understood that the invention is not to be limited to the exact details of construction, operation, exact materials or embodiments shown and described, as obvious modifications and equivalence will be apparent to one skilled in the art; for example, the compartments could be formed as permanent, rigid structures within the housing, and the compartments are selectively filled or emptied of the flowable, radiation blocking material by pumping the flowable, radiation blocking material into, or out of, preselected compartments in lieu of using balloons. Accordingly, the invention is therefore to be limited only by the scope of the appended claims.

What is claimed is:

1. An apparatus for use in conformal radiation therapy of a tumor, comprising:
    (a) a radiation beam source for producing a radiation beam having a predetermined, constant beam intensity;
    (b) at least a 3×3 checkerboard array having alternating radiolucent and radiopaque compartments, for separating the radiation treatment beam into an array of a plurality of beam segments; and
    (c) means for independently modulating the beam intensity of the radiation beam segments to spatially modulate the beam intensity of the radiation treatment beam across the tumor.

2. An apparatus for use in conformal radiation therapy of a tumor, comprising:
    (a) a radiation beam source for producing a radiation beam having a predetermined, constant beam intensity;
    (b) a checkerboard array of a plurality of spaced-apart, radiopaque, compartments having walls, at least a portion of a wall of each of four of the radiopaque compartments defining a radiolucent compartment between the four radiopaque compartments, for separating the radiation treatment beam into an array of a plurality of beam segments; and
    (c) means for independently modulating the beam intensity of the radiation beam segments to spatially modulate the beam intensity of the radiation treatment beam across the tumor.

3. A method of conformal radiation therapy, with a radiation beam having a predetermined, constant beam intensity for treatment of a volume of tissue in a patient, the volume of tissue containing a tumor to be treated, the tumor having a total tumor volume and a varying thickness, comprising the steps of:

(a) directing the radiation treatment beam toward the volume of tissue, (b) separating the radiation treatment beam into an array of at least 3×3 beam segments; and (c) independently modulating the beam intensity of at least one of the beam segments to spatially modulate the beam intensity of the radiation treatment beam across the volume of tissue, to treat the tumor with the beam segments, each radiation beam segment having a predetermined beam intensity.

4. The method of claim 3, including the steps of: (d) rotating the radiation beam about the patient to successively direct the plurality of radiation beam segments toward the volume of tissue; and (e) modulating the beam intensity of the at least one of the radiation beam segments independent of at least one other of the radiation beam segments, to spatially modulate the beam intensity of the radiation treatment beam across the volume of tissue as the plurality of radiation beam segments are directed toward the volume of tissue.

5. The method of claim 4, including the step of rotating the radiation beam in 5 degree segments of a radial arc to treat the volume of tissue after each 5 degrees of rotation of the radiation beam.

6. The method of claim 3, including the step of separating at least one radiation beam into a plurality of radiation beam segments by passing the radiation beam through an array of at least 3×3 compartments extending through a housing, having a top and a bottom, each compartment defining a passageway for a radiation beam segment.

7. The method of claim 3, including the step of separating at least one radiation beam into a plurality of radiation beam segments by passing the radiation beam through an array of at least 3×3 compartments extending through a housing, having a top and a bottom, at least four compartments being closed by radiopaque blocks, having walls, with the radiopaque blocks being disposed in a checkerboard arrangement, the walls of the radiopaque blocks defining at least one radiolucent compartment providing a passageway for a radiation beam segment.

8. The method of claim 7, including the steps of: providing the housing with a quantity of flowable, radiation blocking material in communication with the radiolucent compartments; and the beam intensities of each radiation beam segment are modulated by selectively filling at least a portion of a radiolucent compartment with the flowable, radiation blocking material or removing at least a portion of the flowable, radiation blocking material from a radiolucent compartment.

9. The method of claim 8, including the step of independently varying the amount of time each compartment is selectively filled with the flowable, radiation blocking material.

10. The method of claim 8, including the step of selectively, substantially completely filling a radiolucent compartment with the flowable, radiation blocking material or substantially completely removing the flowable, radiation blocking material from a compartment.

11. The method of claim 8, including the step of utilizing mercury as the flowable, radiation blocking material.

12. The method of claim 8, including the steps of providing an expandable, radiolucent member in each radiolucent compartment; and expanding the radiolucent members within preselected compartments to remove at least a portion of the flowable, radiation blocking material from the preselected compartments.

13. The method of claim 12, including the steps of utilizing inflatable balloons as the expandable, radiolucent members; and expanding the inflatable balloons with a source of pressurized fluid.

14. The method of claim 12, including the steps of: providing each radiolucent compartment with a substantially square cross-sectional configuration; and providing each expandable, radiolucent member, when expanded, with a substantially square cross-sectional configuration substantially conforming to the cross-sectional configuration of the compartments.

15. The method of claim 12, including the steps of: utilizing an integrally formed array of inflatable balloons as the expandable, radiolucent members; and expanding the inflatable balloons with a source of pressurized fluid.

16. The method of claim 14, including the step of: increasing the size of the cross-sectional configuration of each compartment and each expandable, radiolucent member, when expanded, from the top of the housing to the bottom of the housing.

17. The method of claim 16, including the steps of utilizing inflatable balloons as the expandable, radiolucent members; and disposing each inflatable balloon in fluid communication with a source of pressurized fluid.

18. The method of claim 17, including the step of selectively inflating and deflating the inflatable balloons.

19. A method of conformal radiation therapy, with a radiation beam having a predetermined, constant beam intensity for treatment of a volume of tissue in a patient, the volume of tissue containing a tumor to be treated, the tumor having a total tumor volume and a varying thickness, comprising the steps of:

(a) directing the radiation treatment beam toward the volume of tissue;

(b) treating a first portion of the tumor by separating the radiation treatment beam into an array of at least 3×3 beam segments, independently modulating the beam intensity of at least one of the beam segments to spatially modulate the beam intensity of the radiation treatment beam across the volume of tissue, each radiation beam segment having a predetermined beam intensity; and (c) treating a second portion of the tumor by separating the radiation treatment beam into an array of at least 3×3 beam segments, independently modulating the beam intensity of at least one of the beam segments to spatially modulate the beam intensity of the radiation treatment beam across the volume of tissue, each radiation beam segment having a predetermined beam intensity.

20. The method of claim 19, including the steps of: (d) rotating the radiation beam about the patient to successively direct the plurality of radiation beam segments toward the volume of tissue; and (e) modulating the beam intensity of the at least one of the radiation beam segments independent of at least one other of the radiation beam segments, to spatially modulate the beam intensity of the radiation treatment beam across the volume of tissue as the plurality of radiation beam segments are directed toward the volume of tissue.

21. The method of claim 19, including the step of separating at least one radiation beam into a plurality of radiation beam segments by passing the radiation beam through an array of at least 3×3 compartments extending through a housing, having a top and a bottom, each compartment defining a passageway for a radiation beam segment.

22. The method of claim 19, including the step of separating at least one radiation beam into a plurality of radiation beam segments by passing the radiation beam through an array of at least 3×3 compartments extending through a housing, having a top and a bottom, at least four compartments being closed by radiopaque blocks, having walls with the radiopaque blocks being disposed in a checkerboard arrangement, the walls of the radiopaque blocks defining at least one radiolucent compartment providing a passageway for a radiation beam segment.

23. The method of claim 22, wherein the step of treating the second portion of the tumor includes the steps of rotating the array of at least 3×3 compartments 90 degrees and providing the housing with a quantity of flowable, radiation blocking material in communication with the radiolucent compartments, and wherein the beam intensities of each radiation beam segment are modulated by selectively filling at least a portion of a radiolucent compartment with the flowable, radiation blocking material or removing at least a portion of the flowable, radiation blocking material from a radiolucent compartment.

24. The method of claim 22, wherein the step of treating a second portion of the tumor includes the steps of rotating the array of at least 3×3 compartments 180 degrees and providing the housing with a quantity of flowable, radiation blocking material in communication with the radiolucent compartments, and wherein the beam intensities of each radiation beam segment are modulated by selectively filling at least a portion of a radiolucent compartment with the flowable, radiation blocking material or removing at least a portion of the flowable, radiation blocking material from a radiolucent compartment.

25. The method of claim 22, wherein the step of treating a second portion of the tumor includes the steps of shift indexing the array of at least 3×3 compartments and providing the housing with a quantity of flowable, radiation blocking material in communication with the radiolucent compartments, and wherein the beam intensities of each radiation beam segment are modulated by selectively filling at least a portion of a radiolucent compartment with the flowable, radiation blocking material or removing at least a portion of the flowable, radiation blocking material from a radiolucent compartment.

26. An apparatus for use in conformal radiation therapy of a tumor with a radiation beam from a radiation beam source, the radiation beam having a predetermined, constant beam intensity, comprising:

(a) means for separating the radiation treatment beam into a plurality of radiation beam segments, including a housing having a top and a bottom; the housing containing an array of at least 3×3 compartments, extending from the top to the bottom of the housing, each compartment defining a passageway for a radiation beam segment; and (b) means for independently modulating the beam intensity of the plurality of radiation beam segments to spatially modulate the beam intensity of the radiation treatment beam across the tumor.

27. The apparatus of claim 26, wherein the means for separating the radiation treatment beam into a plurality of radiation beam segments includes: a housing having a top and a bottom; the housing containing an array of at least 3×3 compartments, extending from the top to the bottom of the housing, at least four compartments being closed and comprising radiopaque blocks, having walls, in a checkerboard arrangement, the walls of the radiopaque blocks defining at least one open passageway for a radiation beam segment.

28. The apparatus of claim 27, wherein the means for independently modulating the beam intensity of the plurality of radiation beam segments includes: an expandable, radiolucent member associated with each radiolucent compartment; a quantity of flowable, radiation blocking material disposed within the housing and within each radiolucent compartment when the expandable member associated with a radiolucent compartment is unexpanded; and a reservoir for the flowable, radiation blocking material, whereby upon expansion of the expandable member, the expandable member displaces the flowable, radiation blocking material outwardly from the radiolucent compartment associated with the expandable member and into the reservoir, so that a radiation beam segment may pass through the compartment toward a portion of the tumor.

29. The apparatus of claim 28, wherein each compartment has a substantially square cross-sectional configuration and the expandable radiolucent member associated with each radiolucent compartment, when expanded, has a substantially square cross-sectional configuration substantially conforming to the cross-sectional configuration of the radiolucent compartment.

30. The apparatus of claim 29, wherein the size of cross-sectional configuration of each compartment and each expandable, radiolucent member, when expanded, increases from the top of the housing to the bottom of the housing.

31. The apparatus of claim 28, wherein the expandable, radiolucent members are an integrally formed array of inflatable balloons.

32. An apparatus for use in conformal radiation therapy of a tumor with a radiation beam from a radiation beam source, the radiation beam having a predetermined, constant beam intensity, comprising:

(a) a housing having a top and an array of at least 3×3 compartments for separating the radiation treatment beam into a plurality of radiation beam segments; and (b) an integrally formed balloon array, having at least 4 balloons extending into at least 4 compartments.

33. The apparatus of claim 32, wherein the array of at least 3×3 compartments includes a checkerboard array of a plurality of spaced-apart, solid, radiopaque, compartments having walls, at least a portion of a wall of each of four of the solid compartments defining a radiolucent compartment between the four solid compartments, for separating the radiation beam into an array of a plurality of beam segments.

* * * * *